United States Patent
Evans et al.

(10) Patent No.: US 6,706,762 B1
(45) Date of Patent: *Mar. 16, 2004

(54) METHODS FOR THE USE OF INHIBITORS OF CO-REPRESSORS FOR THE TREATMENT OF NEOPLASTIC DISEASES

(75) Inventors: Ronald M. Evans, La Jolla, CA (US); Richard J. Lin, San Diego, CA (US); Laszlo Nagy, San Diego, CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/966,876

(22) Filed: Nov. 10, 1997

Related U.S. Application Data

(63) Continuation-in-part of application No. 08/846,881, filed on May 1, 1997, now Pat. No. 6,387,673.

(51) Int. Cl.$^7$ ............................................. A61K 31/19
(52) U.S. Cl. ..................................................... 514/557
(58) Field of Search ....................... 514/557; 530/387.9, 530/358; 435/7.21, 184, 195, 197; 552/653

(56) References Cited

U.S. PATENT DOCUMENTS

| | | | |
|---|---|---|---|
| 4,690,918 A | * 9/1987 | Beppu et al. | 514/23 |
| 5,091,518 A | 2/1992 | Sucov et al. | 536/23.2 |
| 5,770,613 A | * 6/1998 | Gaeta et al. | 514/332 |

FOREIGN PATENT DOCUMENTS

| | | | |
|---|---|---|---|
| JP | 360149520 | * 8/1985 | |
| WO | WO 92/16546 | 10/1992 | ........... C07H/21/04 |
| WO | 97/35990 | 10/1997 | |

OTHER PUBLICATIONS

Taunton et al. "A mammalian histone deacetylase related to the yeast transcriptional regulator Rpd3p," Science (Apr. 1996) 272:408–411.*

Chen et al. "Retinoic acid is required for and potentiates differentiation of Acute Promyelocytic Leukemia cells by nonretinoid agents," Blood (1994) 84(7): 2122–29, Oct. 1994.*

Chen and Evans, "A transcriptional co–repressor that interacts with nuclear hormone receptors" *Nature* 377:454–457 (1995).

Hörlein, et al., "Ligand–independent repression by the thyroid hormone receptor mediated by a nuclear receptor co–repressor" *Nature* 377:397–404 (1995).

Tallman, M.S., "Differentiating therapy with all–trans retinoic acid in acute myeloid leukemia" *Leikemia* 10 (Suppl. 1):S12–S15 (1996).

Agura, et al., "Identification and Sequence Analysis of the Promoter for the Leukocyte Integrin β–Subunit (CD18): A Retinoic Acid–Inducible Gene" *Blood* 79 (3):602–609 (1992).

Albagli, et al., "The BTB/POZ Domain: A New Protein–Protein Interaction Motif Common to DNA–and Actin–binding Proteins[1]" *Cell Growth & Differentiation* 6:1193–1198 (1995).

Alland, et al., "Role for N–CoR and histone deacetylase in Sin3–mediated transcriptional repression" *Nature* 387:49–55 (1997).

Ayer, et al., "Mad–Max Transcriptional Repression Is Mediated by Ternary Complex Formation with Mammalian Homologs of Yeast Repressor Sin3" *Cell* 80:767–776 (1995).

Baniahmad, et al., "Modular Structure of a Chicken Lysozyme Silencer: Involvement of an Unusual Thyroid Hormone Receptor Binding Site" *Cell* 61:505–514 (1990).

Baniahmad, et al., "The π4 Activation Domain of the Thyroid Hormone Receptor Is Required for Release of a Putative Corepressor(s) Necessary for Transcriptional Silencing" *Molecular and Cellular Biology* 15 (1):76–86 (1995).

Brackman, et al., "Expression of Cell Surface Antigens During the Differentiation of HL–60 Cells Induced by 1,25–Dihydroxyvitamin $D_3$ Retinoic Acid AD DSMO", *Leukemia Research* 94 (1):57–64 (1995).

Brown, et al., "A PMLRARα transgene initiates murine acute promyelocytic leukemia" *Proc. Natl. Acad. Sci. USA* 94:2551–2556 (1997).

Brownell, et al., "Tetrahymena Histone Acetyltransferase A: A Homolog to Yeast Gcn5p Linking Histone Acetylation to Gene Activation" *Cell* 84:843–851 (1996).

Bugge, et al., "RXRα, a promiscuous partner of retinoic acid and thyroid hormone receptors" *The EMBO Journal* 11 (4):1409–1418 (1992).

Casanova, et al., "Functional Evidence for Ligand–Dependent Dissociation of Thyroid Hormone and Retinoic Acid Receptors from an Inhibitory Cellular Factor" *Molecular and Cellular Biology* 14(9):5756–5765 (1994).

(List continued on next page.)

*Primary Examiner*—Jean C. Witz

(57) ABSTRACT

In accordance with the present invention, it has been discovered that histone deacetylase associates with hormone receptor complexes and contributes to the repression thereof. It has further been discovered that exposure of a repressed system to histone deacetylase inhibitors relieves this repression, and that in combination with a ligand for a member the steroid/thyroid superfamily of receptors, the differentiation effects of retinoids are enhanced. Thus, histone deacetylase inhibitors have been found to be useful for the activation of genes responsive to hormone receptors and to conteract the oncogenic functions of oncogenic proteins. In accordance with another aspect of the invention, formulations useful for modulation of hormone-mediated processes have been developed. In addition, assays have been developed for the identification of compounds useful to modulate the above-described processes as well as methods of employing such compounds for the treatment of neoplastic diseases.

16 Claims, 19 Drawing Sheets-

OTHER PUBLICATIONS

Chakravarti, et al., "Role of CBP/P300 in nuclear receptor signalling" *Nature* 383:99–103 (1996).

Chen and Evans, A transcriptional co–repressor that interacts with nuclear hormone receptors *Nature* 377:454–457 (1995).

Chen, et al., "PLZF RARα fusion proteins generated from the variant t(11;17(q23;q21) translocation in accute promyelocytic leukemia inhibit ligand–dependent transactivation of wild–type retinoic acid receptors" *Proc. Natl Acad Sci. USA* 91:1178–1182 (1994).

Chen, et al., "Fusion between a novel *Krüppel*–like zinc finger gene and the retinoic acid receptor–α locus due to a variant t(11;17) translocation associated with acute promyelocytic leukaemia" *The EMBO Journal* 12 (3):1161–1167 (1993).

Chen, et al., "SMRT insoforms mediate repression and anti–repression of nuclear receptor heterodimers" *Proc. Natl. Acad. Sci. USA*. 93:7567–7571 (1996).

Collins, S. J., "Blood" *The Journal of The American Society of Hematology* 70 (5): 1233–1244 (1987).

Damm, et al., "A single point mutation in *erbA* restores the erythroid transforming potential of a mutant avian erythroblastosis virus (AEV) defective in both *erbA* and *erbB* oncogenes" *The EMBO Journal* 6 (2):375–382 (1987).

Damm, et al., "Protein encoded by v–*erbA* functions as a thyroid–hormone receptor antagonist" *Nature* 339 (6226):593–597 (1989).

de Thé, et al., "The PML–RARα Fusion mRNA Generated by the t(15;17) Translocation in Acute Promoyelocytic Leukemia Encodes a Functionally Altered RAR" *Cell* 66: 675–684 (1991).

Dong, et al., "Amino–terminal protein–protein interaction motif (POZ–domain) is responsible for activities of the promyelocytic leukemia zinc finger–retinoic acid receptor–α fusion protein" *Proc. Natl Acad. Sci. USA* 93:3624–3629 (1996).

Dyck, et al., "A Novel Macromolecular Struture Is a Target of the Promyelocyte–Retinoic Acid Receptor Oncoprotein" *Cell* 76:333–343 (1994).

Farsetti, et al., "Characterization of Myelin Basic Protein Thyroid Hormone Response Element and Its Function in the Context of Native and Heterologous Promoter" *The Journal of Biological Chemistry* 267 (22):15784–15788 (1992).

Felsenfeld, G. "Chromatin Unfolds" *Cell* 86:13–19 (1996).

Fondell, et al., "Ligand induction of a transcriptionally active thyroid hormone receptor coactivator complex" *Proc. Natl. Acad. Sci. USA* 93:8329–8333 (1996).

Graf and Beug, "Role of the *v–erbA* and *v–erbB* Oncogenes of Avian Erythroblastosis Virus in Erythroid Cell Transformation" *Cell* 34:7–9 (1983).

Grignani, et al., "Effects on differentiation by the promyelocytic leukemia PML/RARα protein depend on the fusion of the PML protein dimerization and RARα DNA binding domains" *The EMBO Journal* 15 (18):4949–4958 (1996).

Grignani, et al. ,"The Acute Promyelocytic Leukemia–Specific PML–RARα Fusion Protein Inhibits Differentiation and Promotes Survival of Myeloid Precursor Cells" *Cells* 74:423–431 (1993).

Grignani, et al., "Acute Promyelocytic Leukemia: From Genetics to Treatment" *Blood* 83 (1): 10–25 (1994).

Hanstein, et al. ,"p300 is a component of an estrogen receptor coactivator complex" 93:11540–11545 (1996).

Heinzel, et al., "A complex containing N–CoR, mSin3 and histone deacetylase mediates transcriptional repression" *Nature* 387:43–48 (1997).

Hollenberg and Evans, "Multiple and Cooperative *Trans*–Activation Domains of the Human Glucocorticoid Receptor" *Cell* 55:899–906 (1988).

Hörlein, et al., "Ligand–independent repression by the thyroid hormone receptor mediated by a nuclear receptor co–receptor co–repressor" *Nature* 377:397–404 (1995).

Issemann, et al., "The retinoid X receptor enhances the function of the peroxisome proliferator activated receptor" *Biochimie* 75:251–256 (1993).

Janknecht and Hunter, "A growing coactivator network" *Nature* 383:22–23 (1996).

Jansen, et al., "Multimeric complexes of the PML–retinoic acid receptor α fusion protein in acute promyelocytic leukemia cells and interference with retinoid and peroxisome–proliferator signaling pathways" *Proc. Natl Acad. Sci. USA* 92:7401–7405 (1995).

Kakizuka, et al., "Chromosomal Translocation t(15;17) in Human Acute Promyelocytic Leukemia Fuses RARα with a Novel Putative Transcription Factor, PML" *Cell* 66:663–674 (1991).

Kamei, et al., "A CBP Integator Complex Mediates Transcriptional Activation and AP–1 Inhibition by Nuclear Receptors" *Cell* 85:403–414 (1996).

Kastner, et al., "Structure, localization and transcriptional properties of two classes of retinoic acid receptor α fusion proteins in acute promyelocytic leukemia (APL): structural similarities with a new family of oncoproteins" *The EMBO Journal* 11 (2): 629–642 (1992).

Keegan, et al., Separation of DNA Binding from the Transcription–Activating Function of a Eukaryotic Regulatory Protein *Science* 231:699–704 (1986).

Kliewer, et al., "Convergence of 9–*cis* retinoic acid and peroxisome proliferator signalling pathways through heterodimer formation of their receptors" *Nature* 358:771–774 (1992).

Kliewer, et al., "Retinoid X receptor interacts with nuclear receptors in retinoic acid, thyroid hormone and vitamin $D_3$ signalling" *Nature* 355:446–449 (1992).

Kurokawa, et al., "Differential orientations of the DNA–binding domain and carboxy–terminal dimerization interface regulate binding site selection by nuclear receptor heterodimers" *Genes & Development* 7: 1423–1435 (1993).

Ladias, et al., "Regulation of the Apolipoprotein AI Gene by ARP–1, a Novel Member of the Steroid Receptor Superfamily" *Science* 251:561–565 (1991).

Leid, et al., "Purification, Cloning, and RXR Identity of the HeLa Cell Factor with Which RAR or TR Heterodimerizes to Bind Target Sequences Efficiently" *Cell* 68:377–395 (1992).

Licht, et al., "Clinical and Molecular Characterization of a Rare Syndrome of Acute Promyelocytic Leukemia Associated With Translocation (11;17)" *Blood* 85 (4):1083–1094.

Licht, et al., "Reduced and altered DNA–binding and transcriptional properties of the PLZF–retinoic acid receptor–α chimera generated in t(11;17)–associated acute promyelocytic leukemia" *Oncogene* 12:323–336 (1996).

Mangelsdorf and Evans, "The RXR Heterodimers and Orphan Receptors" *Cell* 83:841–850 (1995).

Marks, et al., "H–2RIIBP (RXRβ) heterodimerization provides a mechanism for combinational diversity in the regulation of retinoic acid and thyroid hormone responsive genes" *The EMBO Journal* 11 (4):1419–1435 (1992).

Miyajima, et al., "Identification of two novel members of *erbA* superfamily by molecular cloning: the gene products of the two are highly related to each other" *Nuclear Acids Research* 16 (23): 11057–11074 (1988).

Mlodzik, et al., "The Drosophila *seven–up* Gene, a Member of the Steroid Receptor Gene Superfamily, Controls Photoreceptor Cell Fates" *Cell* 60:211–224 (1990).

Näär, et al., "The Orientation and Spacing of Core DNA–Binding Motifs Dictate Selective Transcriptional Responses to Three Nuclear Receptors" *Cell* 65:1267–1279 (1991).

Nagy, et al., "Activation of Retinoid X Receptors Induces Apoptosis in HL–60 Cell Lines" *Molecular and Cellular Biology* 15 (7):3540–3551 (1995).

Nagy, et al., "Nuclear Receptor Repression Mediated by a Complex Containing SMRT, mSin3A, and Histone Deacetylase" *Cell* 89:3723–380 (1997).

Ogryzko, et al., "The Transcriptional Coactivators p300 and CBP Are Histone Acetyltransferases" *Cell* 87:953–959 (1996).

Oro, et al., "Relationship between the product of the *Drosophila ultraspiracle* locus and the vertebrate retinoid X receptor" *Nature* 347:298–301 (1990).

Perez, et al., "PMLRAR homodimers: distinct DNA binding properties and heteromeric interactions with RXR" *The EMBO Journal* 12 (8): 3171–3182 (1993).

Perlmann, et al., "Determinants for selective RAR and TR recognition of direct repeat HREs" *Genes & Development* 7:1411–1422 (1993).

Raisher, et al., "Identification of a Novel Retinoid–responsive Element in the Promoter Region of the Medium Chain Acyl–Coenzyme A Dehydrogenase Gene" *The Journal of Biological Chemistry* 267 (28):20264–20269 (1992).

Robertson, et al., "Retinoic Acid–Resistant HL–60R Cells Harbor a Point Mutation in the Retinoic Acid Receptor Ligand–Binding Domain That Confers Dominant Negative Activity" *Blood* 80 (80):1885–1889 (1992).

Rousselot, et al., "The PML–RARα gene product of the t(15;17) translocation inhibits retinoic acid–induced granulocytic differentiation and mediated transactivation in human myeloid cells" *Oncogene* 9:545–551 (1994).

Ruthardt, et al., "Opposite Effects of the Acute Promyelocytic Leukemia PML–Retinoic Acid Receptor α (RARα) and PLZF–RARα Fusion Proteins on Retinoic Acid Signalling" *Molecular and Cellular Biology* 17 (8):4859–4869 (1997).

Sande and Privalsky, "Indentification of TRACs ($T_3$ Receptor–Associating Cofactors), a Family of Cofactors That Associate with, and Modulate the Activity of, Nuclear Hormone Receptors" *Molecular Endorcrinology* 10 (7):813–825 (1996).

Sap, et al., "Repression of transcription mediated at a thyroid hormone response element by the v–*erb*–A oncogene product" *Nature* 340:242–244 (1989).

Seol, et al., "Two Receptor Interacting Domains in the Nuclear Hormone Receptor Corepressor RIP13/N–CoR" *Molecular Endocrinology* 10 (12):1646–1655 (1996).

Shao, et al., "A Retinoid–Resistant Acute Promyelocytic Leukemia Subclone Expresses a Dominant Negative PML–RARα Mutation" *Blood* 89(12):4282–4289.

Sladek, et al., "Liver–enriched transciptional factor HNF–4 is a novel member of the steroid hormone receptor superfamily" *Genes & Development* 4:2353–2365 (1990).

Stillman, et al., "Epistasis Analysis of Suppressor Mutations That Allow *HO* Expression in the Absence of the Yeast *SW*15 Transcriptional Activator" *Genetics* 136:781–788 (1994).

Taunton, et al., "A Mammalian Histone Deacetylase Related to the Yeast Transcriptional Regulator Rpd3p" *Science* 272:408–411 (1996).

Tini, et al., "An everted repeat mediates retinoic acid induction of the γF–crystallin gene: evidence of a direct role for retinoids in lens development" *Genes & Development* 7:295–307 (1993).

Towers, et al., "DNA target selectivity by the vitamin $D_3$ receptor: Mechanism of dimer binding to an asymmetric repeat element" *Proc. Natl. Acad. Sci, USA* 90;6310–6314 (1993).

Umesono, et al., "Direct Repeats as Selective Response Elements for the Thyroid Hormone, Retinoic Acid, and Vitamin $D_3$ Receptors" *Cell* 65:1255–1266 (1991).

Umesono, et al., "Retinoic acid and thyroid hormone induce gene expression through a common responsive element" *Nature* 336:262–265 (1988).

Wang, et al., "COUP transcription factor is a member of the steroid receptor superfamily" *Nature* 340:163–166 (1989).

Webster, et al., "The Hormone–Binding Domains of the Estrogen and Glucocorticoid Receptors Contain an Inducible Transcription Activation Function" *Cell* 54:199–207 (1988).

Webster, et al., "The Yeast $UAS_G$ Is a Transcriptional Enhancer in Human HeLa Cells in the Presence of the GAL4 Trans–Activator" *Cell* 52:169–178 (1988).

Weis, et al., "Retinoic Acid Regulates Aberrant Nuclear Localization of PML–RARα in Acute Promyelocytic Leukemia Cells" *Cell* 76:345–356 (1994).

Williams, et al., "Oligomeric Binding of T3 Receptor Is Required for Maximal T3 Response" *The Journal of Biological Chemistry* 266 (29):19636–19644 (1991).

Wolfe and Pruss, "Chromatin: Hanging on to histones" *Curr. Biol.* 6:234–237 (1996).

Yang, et al., "A p300/CBP–associated factor that competes with the adenoviral oncoprotein E1A" *Nature* 382:319–324 (1996).

Yao, et al., "The nuclear hormone receptor coactivator SRC–1 is a specific target of p300" *Proc. Natl. Acad. Sci. USA* 93:10626–10631 (1996).

Yu , et al., "RXRβ:A Coregulator That Enhances Binding of Retinoic Acid, Thyroid Hormone, and Vitamin D Receptors to Their Cognate Response Elements" *Cell*67:1251–1266 (1991).

Zechel, et al., "Dimerization interfaces formed between the DNA binding domains determine the cooperative binding of RXR/RAR and RXR/TR heterodimers to DR5 and DR4 elements" *The EMBO Journal* 13 (6):1414–1424 (1994).

Zhang, et al., "Retinoid X receptor is an auxilliary protein for thyroid hormone and retinoic acid receptors" *Nature* 355:441–446 (1992).

\* cited by examiner

METHODS FOR THE USE OF INHIBITORS OF CO-REPRESSORS FOR THE TREATMENT OF NEOPLASTIC DISEASES

RELATED APPLICATIONS

This application is a continuation-in-part of U.S. Ser. No. 08/846,881, filed May 1, 1997, now U.S. Pat. No. 6,387,673, incorporated by reference herein in its entirety.

FIELD OF THE INVENTION

The present invention relates to methods for the modulation of nuclear receptor mediated processes, compounds useful therefor and methods for the identification and use of such compounds.

BACKGROUND OF THE INVENTION

The actions of steroids, retinoids and thyroid hormones are mediated by intracellular nuclear receptors whose coordinate activity defines the physiological response (Mangelsdorf and Evans, Cell 83:841–850 (1995)). These receptors are all structurally related and constitute a superfamily of nuclear regulatory proteins that modulate gene expression in a ligand-dependent fashion. Previous studies have demonstrated that the 9-cis retinoic acid receptor (RXR) serves as a common heterodimeric partner for thyroid hormone receptor (TR), retinoic acid receptor (RAR), vitamin D receptor (VDR), prostanoids (PPAR), as well as numerous orphan receptors (Kliewer et al. (1992) Nature 355:446–449).

Transcriptional repression is an intrinsic part of endocrine physiology and contributes to feedback regulation associated with the inhibition of the physiologic response. Indeed, the thyroid hormone receptor is converted to an oncogene by mutations which block hormone binding and create a constitutive transcriptional repressor (Damm et al. EMBO J. 6:375–382 (1987), Nature 3:593–597 (1989); Graf and Beug Cell 34:7–9 (1983); Sap et al. Nature 340:242–244 (1989)). Multiple studies on transcriptional silencing by verbA and the non-liganded thyroid hormone receptor suggest that repression is required for oncogenesis and that this process is mediated by a diffusible co-factor(s) that associates with the ligand binding domain (LBD) (Baniahmad et al. Mol. Cell. Biol. 15:76–86 (1995); Casanova et al. Mol. Cell. Biol. 14:1756–1765 (1994)).

Transcriptional co-repressors (SMRT and N-CoR) have recently been identified that associate with non-liganded receptors resulting in suppression of basal transcriptional activity (see, for example, Chen and Evans Nature 377:454–457 (1995); Chen et al. PNAS 93:7567–7571 (1996); Horlein et al. Nature 377:397–404 (1995); and Sande and Privalsky Mol. Endo. 10:813–825 (1996)).

While the mechanism of this repression is not known, chromatin remodeling has been suggested to be a component of transcriptional regulation (for review see Wolffe and Pruss. Curr. Biol. 6:234–237 (1996): Felsenfeld Cell 86:13–19 (1996)). Indeed, it has been suggested that specific transcriptional activation may be involved in local changes in chromatin structure. In fact, it has recently been demonstrated that nuclear hormone receptors may utilize the CREB binding protein (CBP) or its homolog p300 (Janknecht and Hunter Nature 383:22–23 (1996)), to function as a nuclear receptor co-factor (Chakravarti, et al. Nature 383:99–103 (1996); Hanstein et al. PNAS 93:11540–11545 (1996); Kamei et al. Cell 85:403–414 (1996); Yao et al. PNAS 93:10626–10631 (1996)). In addition to CBP/p300, multiple hormone-dependent and independent associated co-factors have been characterized (Fondell et al. PNAS 93:8392–8333 (1996)).

Of particular interest is the recent demonstration that CPB/p300 associates with the histone acetylase P/CAF (Yang X-J et al. Nature 382:319–324 (1996)) which displays significant sequence homology to the yeast transcription activator GCN5, also known to be a histone acetylase (Brownell et al. Cell 84:843–851 (1996)). Further, CBP/p300 harbors intrinsic histone acetyltransferase activity, resulting in alternative or perhaps simultaneous histone acetylation (Ogryzko et al. Cell 87:953–959 (1996)). The notion that multiple transcriptional co-activators possess acetylase activity suggests that their recruitment to a DNA template would locally destabilize nucleosomes, creating a permissive state for promoter activation.

The symptoms of certain neoplastic diseases have been ameliorated by the administration of retinoids. However, some patients afflicted with acute promyelocytic leukemia (APL) respond poorly (if at all), to retinoid differentiation therapy, while others enter disease remission following high doses of retinoic acid treatment. Although APL cell lines have been identified as being retinoid sensitive, there has been no evidence to explain the distinct retinoid responses in APL patients.

Accordingly, there is a need in the art for a further understanding of the interaction(s) between the various components involved in regulation of hormone mediated processes. A clearer understanding of these processes will facilitate the development of methods to modulate hormone mediated processes, as well as assays for the identification of compounds useful for such modulation. Moreover, there is a need in the art for novel approaches for treating human cancer. These and other needs in the art are addressed by the present invention.

BRIEF DESCRIPTION OF THE INVENTION

In accordance with the present invention, we have discovered that histone deacetylase associates with hormone receptor complexes and contributes to the repression thereof. We have further discovered that exposure of a repressed system to histone deacetylase inhibitors relieves this repression. Thus, histone deacetylase inhibitors have been found to be useful for the activation of genes responsive to hormone receptors.

In accordance with another aspect of the invention, formulations useful for modulation of hormone-mediated processes have been developed. In addition, assays have been developed for the identification of compounds useful to modulate the above-described processes. In accordance with another aspect, methods of employing such compounds to modulate or enhance hormone mediated processes, such as human cancers.

In accordance with the present invention, SMRT and components of the histone deacetylase complex have been discovered to function as effectors of cellular transformation. Specifically, the interaction of SMRT with PLZF-RARα and PML-RARα has been discoved to play a critical role in the pathogenesis of acute promyelocytic leukemia (APL). These findings provide the first direct link between nuclear receptor cofactors and human cancer by providing evidence that a transcriptional corepressor may directly contribute to human cancers. Moreover, pharmacological manipulation of the association/dissociation of nuclear receptor cofactors will prove to be beneficial as it provides novel approaches to treatment of human diseases.

DETAILED DESCRIPTION OF THE INVENTION

Figure 1A:
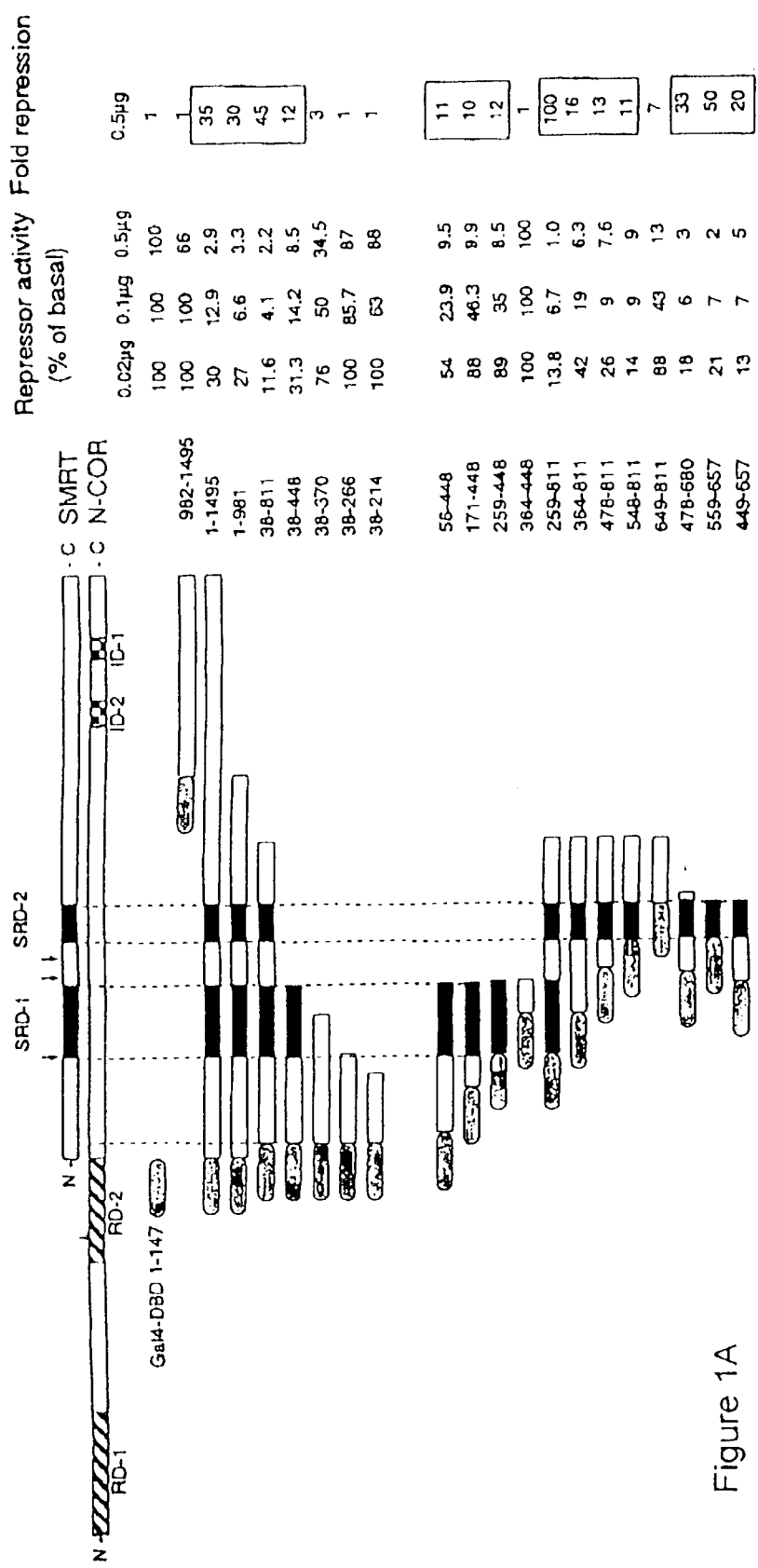
FIG. 1(A) provides a schematic representation showing an alignment of SMRT and N-COR and the boundaries of N- and C-terminal deletion mutants. Hatched boxes indicate the previously identified repressor domains (RD1 and RD2; see Horlein et al., Nature 377:397–404 (1995)) and the checkered boxes indicate the location of receptor interaction domains (ID1 and 2; Seol et al., Mol. Endo. 10:1646–1655 (1996). Arrows indicate the location of bacterial protease digestion sites in SMRT. The GAL4-DNA binding domain (DBD) 1–147 (shaded ovals) was fused to the N-terminus of these constructs and increasing amounts (0.02, 0.1, 0.5 μg) were tested in transient transfection assays for repressor activity (% of the basal activity in the presence of GAL4-DBD only). The minimal repressor domains of SMRT (SRD-1 and SRD-2) are shaded. Repression values of 10 fold or higher are boxed.

In accordance with the present invention, there are provided methods for the modulation of hormone mediated processes in a biological system, said method comprising contacting said system with an amount of a histone deacetylase inhibitor effective to modulate said hormone mediated process.

In a particular aspect of the present invention, there are provided methods of treating a subject with a neoplastic disease comprising administering to the subject an amount of an inhibitor of a co-repressor, preferably inhibitors of histone deacetylase, effective to ameliorate the symptoms of said neoplastic disease. It has been discovered that inhibitors of histone deacetylase counteract the oncogenic function of oncogene peptide(s) and relieve the suppression of basal transcription activity caused by interaction of such oncogene peptides with co-repressors.

Exemplary neoplastic diseases contemplated for treatment employing invention methods include cancer of the breast, bladder, ovary, lung and colon, Burkitt's, astrocytoma, Kaposi's sarcoma, lymphoma, leukemia, and the like. In a presently preferred embodiment, the present method can be employed for the treatment of subjects afflicted with leukemia, including CML and acute leukemia (ANLL and APL).

Inhibitors contemplated for inclusion in the above-described composition include histone deacetylase inhibitors (e.g., Trichostatin A (TSA), Trapoxin, sodium butyrate (NaB), and the like), chromatin remodeling machinery inhibitors, and the like.

As employed herein, the term "oncogene peptide" refers to the protein product of an oncogene, or fragments thereof, capable of inducing one or more characteristics of cancer cells. Exemplary oncogenes include sis, hst, erb B, fms, mas, abl, ras, mos, myc, fos, jun, pml, plzf, laz3/bcl6, and the like. In a presently preferred embodiment, invention methods can be employed to relieve repression caused by oncogene peptides which contain the BTB (Bric-a-brac/Tramtrack/Broad Complex; see, e.g., Albagli et al. *Cell Growth &*

*Differentiation* 6:1193–1198 (1995)) domain and/or recruit the co-repressor SMRT to repress transcription. Examples of such oncogene peptides include PLZF, LAZ3/BCL6, PML, and the like.

In a particular aspect of the present invention, the oncogene peptide is an oncogenic fusion protein wherein the oncogene product, or fragment thereof, is operatively associated with a member of the steroid/thyroid hormone superfamily of receptors. Examples of such oncogenic fusion proteins include PML-RARα and PLZF-RARα. The t(15;17) or t(11;17) chromosomal translocations that fuse either PML (Kakizuka et al. (1991) *Cell* 66:663–674; de Théet al. (1991) *Cell* 66:675–684; Kastner et al. (1992) *EMBO J*. 11:629–642) or PLZF (Chen et al. (1993) *EMBO J*. 12:1161–1167; Chen et al. (1994) *Proc. Natl Acad. Sci. USA* 91:1178–1182), respectively, to the retinoic acid receptors (RARα) are cytogenetic hallmarks of acute promyelocytic leukemia (APL). Both PML-RARα and PLZF-RARα chimeric proteins are oncogenic and dominant negative inhibitors of retinoid signaling (Chen et al. (1994) *Proc. Natl Acad. Sci. USA* 91:1178–1182; Licht et al. (1996) *Oncogene* 12:323–336; Grignani et al. (1993) *Cell* 74:423–431).

Clinically, t(15;17) patients enter disease remission following high doses of retinoic acid treatment, while t(11;17) patients respond very poorly if at all (Licht et al. (1995) *Blood* 85:1083–1094). Both fusion proteins associate with the nuclear receptor co-repressor SMRT (Chen et al. (1995) *Nature* 377:454–457) and the histone deacetylase complex (Nagy et al. (1997) *Cell* 89:373–380; Heinzel et al. (1997) *Nature* 387:43–48; Alland et al. (1997) *Nature* 387:49–55). PLZF-RARα binds retinoic acids (RA) with affinity similar to RAR. In accordance with the present invention, it has been discovered that inhibition of SMRT-mediated repression restores retinoid responsiveness to PLZF-RARα. Based on this observation, it is believed that ligand-insensitive association of SMRT with the PLZF moiety of PLZF-RARα underlies the retinoid non-responsiveness.

As employed herein, the term "modulate" refers to the ability of a modulator for a member of the steroid/thyroid superfamily to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

As employed herein, the phrase "hormone mediated processes" refers to biological, physiological, endocrinological, and other bodily processes which are mediated by receptor or receptor combinations which are responsive to the ligands described herein. Modulation of such processes can be accomplished in vitro or in vivo. In vivo modulation can be carried out in a wide range of subjects, such as, for example, humans, rodents, sheep, pigs, cows, and the like. Exemplary processes contemplated to be modulated include neoplastic diseases, inflammatory or infectious diseases, and the like.

As employed herein, the phrase "biological system" refers to an intact organism or a cell-based system containing the various components required for response to the ligands described herein, e.g., an isoform of RAR (i.e., RARα, RARβ or RARγ), a silent partner for the RAR isoform (e.g., RXR), and an RAR-responsive reporter (which typically comprises an RAR response element (RARE) in operative communication with a reporter gene; suitable reporters include luciferase, chloramphenicol transferase, γ-galactosidase, and the like.

Contacting in a biological system contemplated by the present invention can be accomplished in a variety of ways, and the treating agents contemplated for use herein can be administered in a variety of forms (e.g., in combination with a pharmaceutically acceptable carrier therefor) and by a variety of modes of delivery. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

As employed herein, the phrase "effective amount" refers to levels of compound sufficient to provide circulating concentrations high enough to modulate the expression of gene(s) mediated by members of the steroid/thyroid superfamily of receptors. Such a concentration typically falls in the range of about 10 nM up to 2 μM; with concentrations in the range of about 100 nM up to 500 nM being preferred. Since the activity of different compounds described herein may vary considerably, and since individual subjects may present a wide variation in severity of symptoms, it is up to the practitioner to determine a subject's response to treatment and vary the dosages accordingly.

Histone deacetylase enzymes contemplated for use in the practice of the present invention include HDAC1, Rpd3, and the like.

In a presently preferred aspect of the present invention, a ligand for a member of the steroid/thyroid superfamily of receptors is administered to said system in addition to said histone deacetylase inhibitor.

As employed herein, the term "ligand (or ligand precursor) for a member of the steroid/thyroid hormone superfamily of receptors" (i.e., intracellular receptor) refers to a substance or compound which, in its unmodified form (or after conversion to its "active" form), inside a cell, binds to receptor protein, thereby creating a ligand/receptor complex, which in turn can activate an appropriate hormone response element. A ligand therefore is a compound which acts to modulate gene transcription for a gene maintained under the control of a hormone response element, and includes compounds such as hormones, growth substances, non-hormone compounds that modulate growth, and the like. Ligands include steroid or steroid-like compounds, retinoids, thyroid hormones, pharmaceutically active compounds, and the like. Individual ligands may have the ability to bind to multiple receptors.

As employed herein, the phrase "members of the nuclear receptor superfamily" (also known as "members of the steroid/thyroid superfamily of receptors" or "intracellular receptors") refers to hormone binding proteins that operate as ligand-dependent transcription factors, including identified members of the steroid/thyroid superfamily of receptors for which specific ligands have not yet been identified (referred to hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66–68 amino acid residues, and possessing about 20 invariant amino acid residues, including nine cysteines.

A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153). The highly conserved amino acids of the DNA-binding domain of members of the superfamily are as follows:

Cys - X - X - Cys - X - X - Asp* - X -
Ala* - X - Gly* - X - Tyr* - X - X -
X - X - Cys - X - X - Cys - Lys* -
X - Phe - Phe - X - Arg* - X - X - X -
X - X - X - X - X - X - (X - X -) Cys
-X - X - X - X - X - (X - X - X -) Cys
-X - X - X - Lys - X - X - Arg - X - X
-Cys - X - X - Cys - Arg* - X - X -
Lys* - Cys - X - X - X - Gly* - Met
(SEQ ID NO: 1);

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors include steroid receptors such as glucocorticoid receptor, mineralocorticoid receptor, progesterone receptor, androgen receptor, vitamin $D_3$ receptor, and the like; plus retinoid receptors, such as RARα, RARβ, RARγ, and the like, plus RXRα, RXRβ, RXRγ, and the like; thyroid receptors, such as TRα, TRβ, and the like; as well as other gene products which, by their structure and properties, are considered to be members of the superfamily, as defined hereinabove. Examples of orphan receptors include the PPARs (e.g., PPARα, PPARγ and PPARδ), HNF4 [see, for example, Sladek et al., in *Genes & Development* 4:2353–2365 (1990)], the COUP family of receptors [see, for example, Miyajima et al., in *Nucleic Acids Research* 16:11057–11074 (1988), Wang et al., in *Nature* 340:163–166 (1989)], COUP-like receptors and COUP homologs, such as those described by Mlodzik et al., in *Cell* 60:211–224 (1990) and Ladias et al., in *Science* 251:561–565 (1991), the ultraspiracle receptor [see, for example, Oro et al., in *Nature* 347:298–301 (1990)], and the like.

The retinoic acid receptor (RAR), the thyroid hormone receptor ($T_3R$), the vitamin $D_3$ receptor (VDR) and the fatty acid/peroxisome proliferator activated receptor (PPAR), for example, preferentially bind to DNA as heterodimers with a common partner, the retinoid X (or 9-cis retinoic acid) receptor (RXR; see, for example, Yu et al., in *Cell* 67:1251–1266 (1991); Bugge et al., in *EMBO J.* 11:1409–18 (1992); Kliewer et al., in *Nature* 355:446–449 (1992); Leid et al, in *Cell* 68:377–395 (1992); Marks et al., in *EMBO J.* 11:1419–1435 (1992); Zhang et al., in *Nature* 355:441–446 (1992); and Issemann et al., in *Biochimie*. 75:251–256 (1993).

In accordance with another embodiment of the present invention, there are provided compositions comprising:

(a) a ligand for a member of the steroid/thyroid hormone superfamily of receptors, and (b) an inhibitor for co-repressor(s) which interact with said member of the steroid/thyroid hormone superfamily of receptors to suppress basal transcription activity in a pharmaceutically acceptable carrier therefor.

Presently preferred ligands contemplated for inclusion in the above-described compositions are ligands for retinoid receptors (e.g., all-trans retinoic acid, 9-cis retinoic acid, and the like), ligands for thyroid hormone receptors (e.g., thyroid hormone), or ligands for vitamin $D_3$ receptor (e.g., 1,25-dihydroxy vitamin D), and the like.

In accordance with another embodiment of the present invention, there are provided isolated co-repressor complexes comprising:

(i) at least one co-repressor, (ii) a histone deacetylase, and (iii) a homodimer or heterodimer of a member of the steroid/thyroid superfamily of receptors.

As employed-herein, the phrase "isolated" refers to peptides which have been removed from their native environment, either by enrichment thereof from natural sources, by chemical synthesis, by recombinant production, and the like. Thus, the recombinant expression of the above-described co-repressor complex would produce an "isolated" protein complex, since such expression would produce the peptide in a non-native environment. Similarly, substantial enrichment of the co-repressor complex content of a cell extract would also provide an "isolated" peptide complex.

Co-repressors contemplated by the above-described complexes include co-repressor(s) having a structure and function characteristic of SMRT (i.e., silencing mediator for retinoic acid and thyroid receptors), repressor domains of SMRT (e.g., SRD-1, SRD-2, amino acids 1–981 thereof, and the like), mSin3A, protein-protein interaction domains of mSin3A (e.g., PAH-1, PAH-2, PAH-3, PAH-4, combinations of PAH, and the like), N-CoR, Mad/Mxi-1, mSin3B, Sin3, histone deacetylase enzymes, and the like, as well as combinations of any two or more thereof.

As is known in the art, there are a number of histone deacetylase enzymes known in the art, any of which can be included in the above-described complexes, e.g., HDAC1, Rpd3, and the like.

The co-repressor complex is a critical component of switches which control cell cycle regulation and cancer. For example, co-repressor complexes function as integrators in multiple transcriptional regulatory pathways to control cell growth and differentiation. Transcriptional co-repressors such as SMRT and N-CoR associate with non-liganded receptors resulting in suppression of basal transcriptional activity (Chen and Evans *Nature* 377:454–457 (1995); Chen et al. *PNAS* 93:7567–7571 1996; Horlein et al. *Nature* 377:397–404 (1995); Sande and Privalsky *Mol Endo*

10:813–825 (1996). In contrast, mSin3A associates with Mad/Mxi-1:Max heterodimers to promote differentiation (Ayer et al. *Cell* 80:767–776 (1995)). Thus, in accordance with the present invention, compounds are contemplated which promote dissociation of the co-repressor complex from hormone receptors (e.g., retinoid and/or thyroid hormone receptors) and further promote association of co-repressor complexes with Mad/Mxi-1 growth inhibitors.

As used herein, the term "homodimer/heterodimer" refers to a homodimeric or heterodimeric form of one or more members of the steroid/thyroid hormone superfamily of receptors, wherein at least one of said members contains a silencing domain which represses basal level promoter activity of target genes. Homodimeric or heterodimeric members of the steroid/thyroid hormone superfamily of receptors contemplated for use herein include thyroid hormone receptor homodimer, thyroid hormone receptor-retinoid X receptor heterodimer, retinoic acid receptor homodimer, retinoic acid receptor-retinoid X receptor heterodimer, retinoid X receptor homodimer, and the like.

In accordance with still another embodiment of the present invention, there are provided methods to identify compounds which disrupt complex comprising:

(i) at least one co-repressor,
(ii) a histone deacetylase, and
(iii) a homodimer or heterodimer of a member of the steroid/thyroid superfamily of receptors,
said method comprising:
 (a) contacting a modified host cell with a test compound, wherein said modified host cell comprises:
  a first fusion protein comprising a GAL4 DNA binding domain (or, in an alternative embodiment, an activation domain), operatively associated with at least one co-repressor,
  a second fusion protein comprising an activation domain (or, in an alternative embodiment, a GAL4 DNA binding domain), operatively associated with a histone deacetylase, and
  a reporter construct comprising a GAL4 response element operatively linked to a reporter gene; and
 (b) selecting those test compounds which cause reduced expression of the reporter gene product.

As used herein, the term "disrupt" embraces compounds which cause substantially complete dissociation of the various components of the complex, as well as compounds which merely alter the conformation of one or more components of the complex so as to reduce the repression otherwise caused thereby.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37° C.

Various constructs employed in the practice of the present invention are well known in the art. Thus, the GAL4 DNA binding domain, the activation domain, GAL4 response elements and various members of the basal transcription machinery have all been well characterized and extensively discussed in the art. For example, the DNA binding domain of the yeast GAL4 protein comprises at least the first 74 amino acids thereof (see, for example, Keegan et al., *Science* 231:699–704 (1986)). Preferably, the first 90 or more amino acids of the GAL4 protein will be used, with the first 147 amino acid residues of yeast GAL4 being presently most preferred.

Activation domains contemplated for use in the practice of the present invention are well known in the art and can readily be identified by the artisan. Examples include the GAL4 activation domain, BP64, VP16, and the like.

Exemplary GAL4 response elements are those containing the palindromic 17-mer:
 5'-CGGAGGACTGTCCTCCG-3' (SEQ ID NO:2), ps such as, for example, 17MX, as described by Webster et al., in *Cell* 52:169–178 (1988), as well as derivatives thereof. Additional examples of suitable response elements include those described by Hollenberg and Evans in *Cell* 55:899–906 (1988); or Webster et al. in *Cell* 54:199–207 (1988).

Exemplary reporter genes include chloramphenicol transferase (CAT), luciferase (LUC), beta-galactosidase (β-gal), and the like.

As used herein, the phrase "operatively associated with" means that the respective DNA sequences (represented, for example, by the terms "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the corresponding "response element" was "turned on" or otherwise activated.

As readily recognized by those of skill in the art, the above-described assay can be modified to facilitate identification of compounds which disrupt any of the specific interactions involved in the formation of the above-described complex.

In accordance with yet another embodiment of the present invention, there are provided methods to identify compounds which disrupt complex comprising:

(i) at least one co-repressor,
(ii) a histone deacetylase, and
(iii) a homodimer or heterodimer of a member of the steroid/thyroid superfamily of receptors,
and optionally also activate said member, said method comprising:
 (a) contacting a modified host cell with a test compound, wherein said modified host cell comprises:
  a first fusion protein comprising an activation domain, operatively associated with at least one co-repressor,
  a second fusion protein comprising a GAL4 DNA binding domain, operatively associated with a histone deacetylase, a first reporter construct comprising a GAL4 response element operatively linked to a first reporter gene, and a second reporter construct comprising a hormone response element operatively linked to a second reporter gene; and (b) identifying those test compounds which cause reduced expression of the first reporter gene product and increased expression of the second reporter gene product as compounds which both disrupt said complex and activate said member, and identifying those test compounds which cause reduced expression of the first reporter gene product, but substantially no change in the level of expression of the second reporter gene product as compounds which disrupt said complex, but do not activate said member.

Those of skill in the art can readily determine suitable hormone response elements (HREs) for use in the practice of the present invention, such as, for example, the response elements described in U.S. Pat. No. 5,091,518 and PCT published application No. WO 92/16546, both of which are hereby incorporated by reference herein.

Naturally occurring HREs are composed of direct repeats (i.e., DRs; see Umesono et al., in *Cell* 65:1255–1266 (1991), inverted repeats (i.e., IRs; see Umesono et al., in *Nature* 336:262–265 (1988), and Williams et al. in *J. Biol. Chem.* 266:19636–19644 (1991)), and/or everted repeats (ERs; see Baniahmad et al., in *Cell* 61:505–514 (1990); Farsetti et al., in *J.-Biol. Chem.* 267:15784–15788 (1992); Raisher et al., in *J. Biol. Chem.* 267:20264–20269 (1992); or Tini et al., in *Genes Dev.* 7:295–307 (1993)) of a degenerate $X_n$-AGGTCA core-site.

In direct repeats (DR, head-to-tail arrangement), the $X_n$ sequence also serves as a gap which separates the two core-binding sites. Thus, for example, spacers of 1, 3, 4 and 5 nucleotides serve as preferred response elements for heterodimers of RXR with PPAR, VDR, T$_3$R and RAR, respectively (see, for example, Naar et al., in *Cell* 65:1267–1279 (1991); Umesono et al., 1991, supra; Kliewer et al., in *Nature* 358:771–774 (1992); and Issemann et al., supra,) The optimal gap length for each heterodimer is determined by protein-protein contacts which appropriately position the DNA binding domains (DBDs) of RXR and its partner (see, for example, Kurokawa et al. *Genes Dev.* 7:1423–1435 (1993); Perlmann et al. *Genes Dev.* 7:1411–1422 (1993); Towers et al. *Proc. Natl. Acad. Sci. USA* 90:6310–6314 (1993); and Zechel et al. *EMBO J.* 13:1414–1424 (1994)).

Direct repeat hormone response elements (HREs) contemplated for use in the practice of the present invention are composed of at least one direct repeat of two or more half sites, optionally separated by one or more spacer nucleotides (with spacers of 1–5 preferred) The spacer nucleotides can be selected from any one of A, C, G or T. Each half site of direct repeat HREs contemplated for use in the practice of the invention comprises the sequence.

—RGBNNM—, wherein

R is selected from A or G;

B is selected from G, C, or T;

each N is independently selected from A, T, C, or G; and

M is selected from A or C;

with the proviso that at least 4 nucleotides of said —RGBNNM—sequence are identical with the nucleotides at corresponding positions of the sequence —AGGTCA—. Response elements employed in the practice of the present invention can optionally be preceded by $N_x$, wherein x falls in the range of 0 up to 5.

In accordance with a still further aspect of the present invention, there are provided methods to identify compounds which prevent disruption of complex comprising:

(i) at least one co-repressor, (ii) a histone deacetylase, and (iii) a homodimer or heterodimer of a member of the steroid/thyroid superfamily of receptors, said method comprising:

(a) contacting a modified host cell with a test compound in the presence of a ligand for said member of the steroid/thyroid superfamily of receptors, wherein said modified host cell comprises:

a first fusion protein comprising a GAL4 DNA binding domain (or, in an alternative an activation domain), operatively associated with at least one co-repressor, a second fusion protein comprising an activation domain (or, in an alternative a GAL4 DNA binding domain), operatively associated with a histone deacetylase, and a reporter construct comprising a GAL4 response element operatively linked to a reporter gene; and (b) selecting those test compounds which prevent ligand-induced reduction of expression of the reporter gene product.

As readily understood by those of skill in the art, a wide variety of compounds can be assayed employing the invention method. Any compound with the potential to act as a ligand can be tested, e.g., steroid or steroid-like compounds, retinoids, thyroid hormones, pharmaceutically active compounds, naturally occurring compounds, synthetic organic compounds, and the like.

In accordance with yet another embodiment of the present invention, there are provided methods to identify compounds which disrupt complex comprising:

(i) at least one co-repressor, (ii) a histone deacetylase, and (iii) a homodimer or heterodimer of a member of the steroid/thyroid superfamily of receptors, said method comprising:

(a) contacting an affinity matrix with a test compound, wherein said affinity matrix comprises:

an affinity support, a first fusion protein comprising a member of the steroid/thyroid hormone superfamily of receptors, operatively associated with a glutathione-S-methionine (GST) label (or, in an alternative embodiment, a HIS label), a second fusion protein comprising a heterologous partner for said member, operatively associated with a HIS label (or, in an alternative embodiment, a GST label), and at least one co-repressor; and (b) selecting those test compounds which cause the release of co-repressor from said support.

In accordance with still another embodiment of the present invention, there are provided methods to identify modulators for members of the steroid/thyroid hormone superfamily of receptors, said method comprising:

(a) contacting a host cell with a co-repressor inhibitor and a test compound,
   wherein said host cell expresses said member of the steroid/thyroid hormone superfamily of receptors, and wherein said host cell optionally contains a reporter construct comprising a hormone response element operatively linked to a reporter gene; and
(b) identifying as modulators those test compounds which modulate expression of gene product(s) under the control of said member.

The invention will now be described in greater detail by reference to the following non-limiting examples.

EXAMPLE 1

Preparation of Plasmids, Antibodies and Chemicals

The following plasmids have been described: CMX-SMRT; CMX-C-SMRT; CMX-N-SMRT and CMXGAL-C-SMRT (Chen et al. (1995) Nature 377: 454–457); CMX-PML-RARα (Kakizuka et al. (1991) Cell 66:663–674); CMXGAL-mSin3A (PAH1–4; Nagy et al. (1997) Cell 89:373–380) pSG5-PLZF and pSG5-PLZF-RARα (Chen et al. (1994) Proc. Natl Acad. Sci. USA 91:1178–1182); pSG5-pML-RARα (m4; Shao et al. (1997) Blood 89:4282–4289); HA-RARα (amino acids 61–462), HA-PLZF and HA-PLZF-RARα were constructed by PCR to incorporate a HA tag at the 5' end of corresponding cDNA sequence and cloned into pCMX. SMRT deletion mutants and GST fusions were cloned into pCMX and pGEX-KG respectively. VP-PML-RARα was generated by fusion of corresponding cDNA sequence to VP16-AD in CMX-VP16. CMX-hRARα 411 was constructed by introduction of a stop codon at amino acid 411 of human RARα (Robertson et al. (1992) Blood 80:1885–1889) using Quick-change mutagenesis kit (Stratagene). All PCR derived products were verified by sequencing.

The anti-SMRT polyclonal antibody used for immunoblotting was produced in a rabbit injected with purified GST-SMRT (amino acids 38–448) proteins. Rabbit anti-SMRT antibody used for immunofluorescence has been described (Chen et al. (1996) Proc. Natl Acad Sci. USA. 93:7567–7571). Mouse anti-HA (12CA5) antibody was purchased from Boehringer Mannheim. Goat AP-conjugated secondary antibodies were purchased from BioRad. Donkey FITC-conjugated anti-mouse or Texas-Red-conjugated anti-rabbit antibodies were from Jackson ImmunoResearch Laboratory. Histone deacetylase inhibitors were obtained from CalBiochem (sodium butyrate) and Waco Pure Chemical Industries (TSA).

EXAMPLE 2

SMRT has Two Independent Repressor Domains

The silencing activity of SMRT resides in the N-terminal half (amino acids 1–981) of the protein, while the receptor interaction domain (ID) is in the remaining C-terminal segment (Chen and Evans, Nature 377:454–457 (1995)). Minimal, transferable repressor domain(s) were identified in order to understand the mechanism of transcriptional repression and its molecular basis. Mammalian expression vectors expressing SMRT, SMRT 982–1495 (C-SMRT), SMRT 1–981 (N-SMRT), GAL4-SMRT, GAL4-SMRT 1–981, GAL4-SMRT 982–1495, pCMX GAL4-DBD, pCMX-VP16, pMH100 TK-luc have been described previously (Chen and Evans, Nature 377:454–457 (1995)). SMRT-GAL4 constructs were generated by PCR amplification of the indicated regions and fused to GAL4 DNA binding domain (DBD) 1–147 (FIG. 1A). Plasmids were constructed by standard techniques.

Repressor activity was determined by transiently transfecting into CV-1 cells increasing amounts of the GAL4-fusion vectors along with a reporter construct pMH-100 TK-luc which contains 4 GAL4 binding sites. (Chakravarti et al., Nature 383:99–103 (1996)). Fold repression was determined relative to the basal transcriptional activity of the reporter in the presence of GAL4 DBD alone. Luciferase activity of each sample was normalized by the level of β-galactosidase activity. Each transfection was carried out in triplicate and repeated 3–6 times. Yeast transformation and β-galactosidase activity assays were carried out in strain Y190 according to manufacturers protocol (Clonetech). The results of this assay are illustrated in FIG. 1A.

SMRT 38–811 appears to be as potent a repressor (45 fold) as either full length SMRT (35 fold) or SMRT 1–981 (30 fold), suggesting that in fact it contains all the domains necessary for full repression. Additional nested C-terminal deletions revealed a smaller though less potent repressor domain, SMRT 38–448 (12 fold). Further C-terminal deletions significantly lowered (38–370, 2.8 fold) and abolished (38–266) repressor activity. N-terminal deletions of SMRT 38–448 revealed that the minimal repressor domain resides between amino acids 259–448 (12-fold repression). Further deletions abolished the repressor activity (364–448). Thus, amino acids 259–448 define an autonomous SMRT repressor domain (SRD-1).

That SRD-1 is a structural domain is supported by the observation that there were several sites susceptible to protease digestion by bacterial proteases in the vicinity of the boundaries of SRD-1 (see FIG. 1A arrows). Expanding SRD-1 towards the C-terminus (259–811) yielded a construct with increased repressor activity (100-fold) suggesting the presence of a second repressor domain. Additional deletions localized the boundary of a second, autonomous minimal repressor domain between amino acids 559–657 (50 fold repression) which is termed SRD-2. SRD-1 and SRD-2 share substantial homology with the comparable region in N-CoR (42% and 39%, respectively) suggesting functional conservation.

EXAMPLE 3

Interaction Between SMRT and mSin3A

Figure 1B:
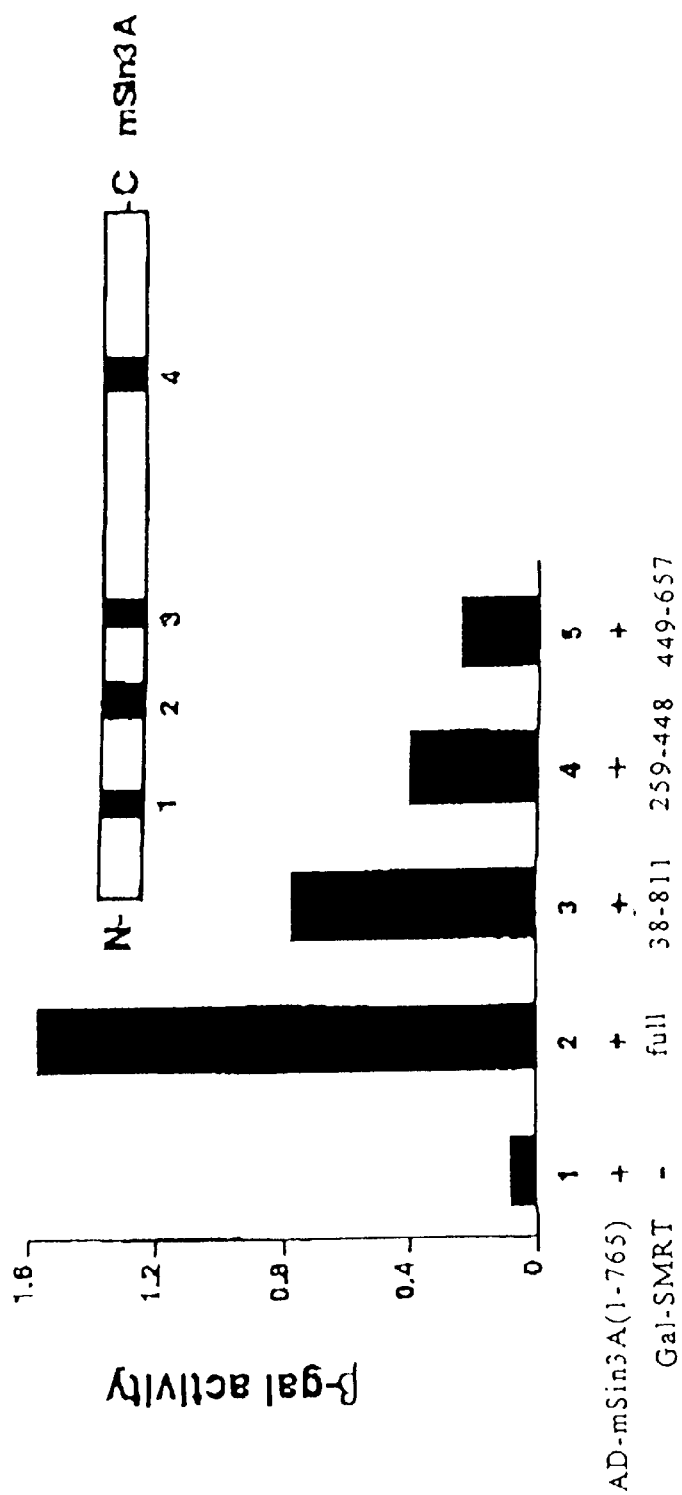
FIG. 1(B) illustrates the interaction of SMRT with mSin3A in yeast. Mean values of at least 6 independent measurements are presented. Also illustrated is a schematic representation of mSin3A with amphipathic helix (PAH) domains (1–4) shown as boxes.

To explore the possibility of the existence of a SMRT-repressor complex that may involve mSin3A, several protein based interaction assays were utilized. The yeast two-hybrid system was used to demonstrate functional association and to map the potential interface between SMRT and mSin3A (FIG. 1B). The above-described fragments of SMRT fused to GAL4 DNA binding domain (GAL4-DBD, Example 1) were co-transformed with GAL4 activation domain fused to mSin3A (AD-mSin3A) into yeast cells. β-galactosidase activity from 3 independent transformants was determined as described above (Example 1). When fused to mSin3A, the GAL4 activation domain (AD) gives a low background reporter activity. However, in the presence of the GAL4 DNA binding domain (GAL4 DBD) fusion to intact SMRT (GAL4-SMRT), high reporter activity was observed, indicating a strong association between SMRT and mSin3A.

Utilizing a series of deletion mutants, association with mSin3A was mapped to two regions of SMRT, amino acids 259–448, which correspond to SRD-1 and amino acids 449–657, which corresponds to SRD-2, respectively. Consistent with the domain mapping, further deletions (38–214, 38–266, and 336–370) completely abolish association with mSin3A. Therefore, these results suggest that the repressor activities of SRD1 and SRD2 are mediated via association with mSin3A.

Figure 1C:
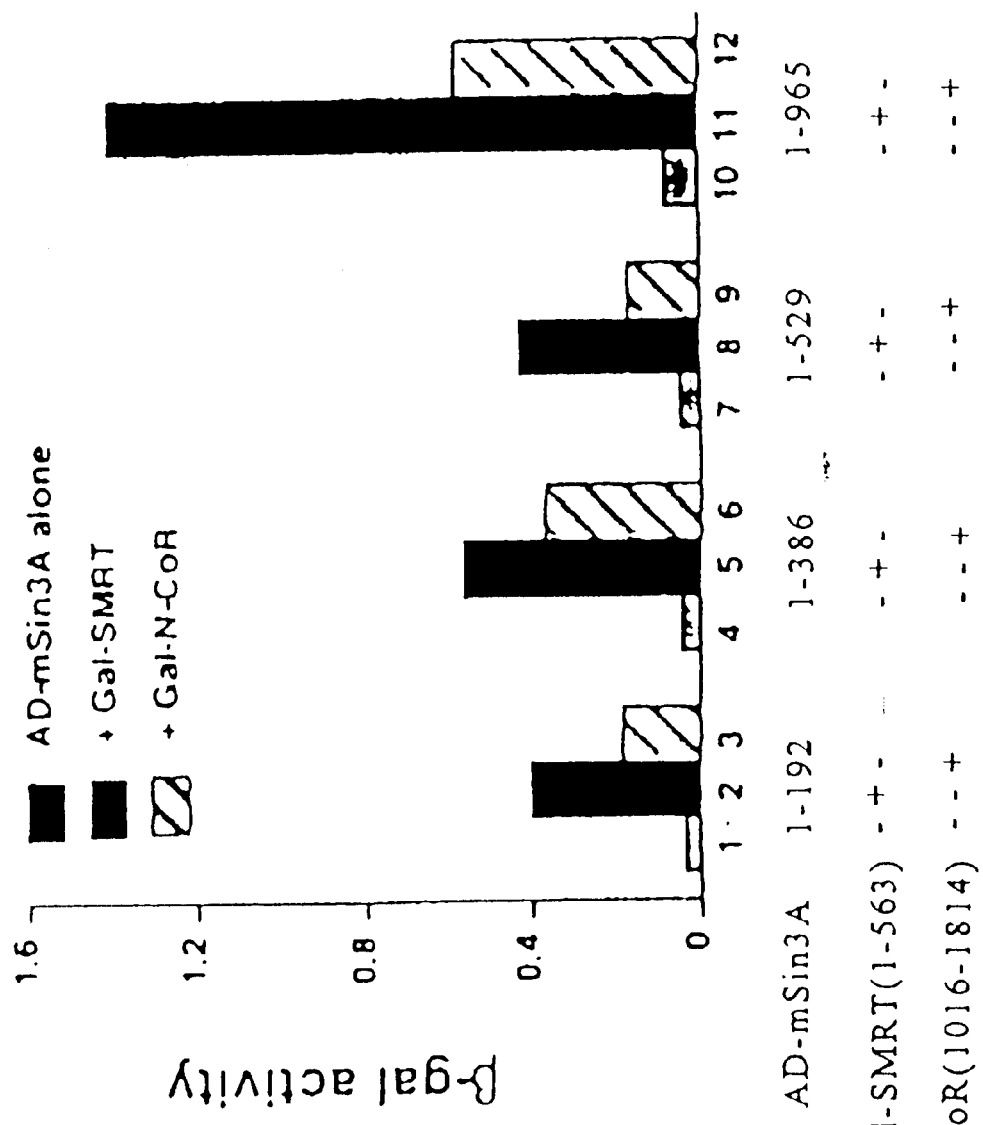
FIG. 1(C) diagrams the interaction of mSin3A with SMRT and N-CoR.

A reciprocal set of experiments was conducted utilizing GAL4 DBD fusions of the SMRT repressor domain to various deletions of mSin3A (FIG. 1C). C-terminal deletions of mSin3A were fused to the GAL4 activation domain and co-transformed individually with either GAL4-SMRT (1–563) or GAL4-N-CoR (1016–1814) into yeast cells. β-galactosidase activity was determined as described above (Example 1). Amino acid sequence 1–192 contains amphipathic helix (PAH) domain 1 (PAH1); 1–386 contains both PAH domains 1 and 2; 1–529 contains PAH domains 1, 2, and 3; and 1–965 contains all four PAH domains plus the conserved linker between PAH 3 and 4.

These experiments show that PAH1 of mSin3A mediates interaction with SMRT while PAH2, 3 or 4 alone show no autonomous association. Inclusion of PAH1 and 2 results in a stronger association while addition of PAH3 shows no additional benefit. The strongest association is observed when all four PAHs are included. This indicates that SMRT makes extensive contacts with mSin3A. This is in contrast to Mad/Mxi-1 which selectively bind PAH2 via a 25 amino acid N-terminal segment.

The SMRT-related co-repressor, N-CoR, was also examined to determine if it associates with mSin3A via SRD-1 and SRD-2 related regions. While the boundaries of these regions have not been determined in detail, results indicate that N-CoR also interacts with mSin3A.

EXAMPLE 4

A SMRT mSin-3A, HDAC 1 Ternary Complex

To determine if these interactions are direct, GST fusion proteins of 38–266, 38–448 and 548–811 of SMRT were examined for their ability to bind in vitro translated $^{35}$S-Methionine-labeled mSin3A in pull down experiments. GST-SMRT 38–266, 38–448 and 548–811 were purified from E.coli cells and extracts were passed through a Glutathione Sepharose 4B affinity column (Pharmacia). Bound proteins were eluted with 15 mM glutathione. Purified proteins were re-bound to Glutathione Sepharose beads and used as affinity matrices. In vitro translated, $^{35}$S Methionine labeled mSin3A was incubated with GST, GST-SMRT 38–266 or GST-38–448. Only GST-SMRT-38–448 but not GST-SMRT 38–266 or GST alone pulls down radiolabeled mSin3A. These results suggest the existence of a direct physical interaction between SRD-1 and mSin3A.

mSin3A and B were compared for their ability to interact with SRD-1. In vitro translated, $^{35}$S Methionine labeled mSin3A, mSin3B and PAH domains of mSin3A (PAH1 (112–192), PAH1-2 (112–386), PAH1-3 (112–529), PAH1-4 (112–965) were used as probes in GST pull down experiments as described above with GST-SMRT 38–448 (S) or GST (G)). No interaction was detected between SMRT and mSin3B under conditions in which mSin3A shows strong association. This experiment suggests that there may be a marked functional difference between the mSin3A and B isoforms.

Next, the region of mSin3A which mediates the observed association with SRD-1 was determined. When radiolabeled PAH 1, 1–2 and 1–3 were tested in the same assay no apparent interaction was seen as with the yeast two-hybrid experiment. However, when all PAH domains (1–4) were included, strong interaction was observed.

Given that unliganded RAR/RXR heterodimers interact with SMRT and SMRT interacts with mSin3A, one would predict a hormone sensitive complex of all four proteins should form in vitro. To test this prediction, an affinity matrix consisting of GST-tagged RXR and His-tagged RAR bound to glutathione beads was used in pull down experiments. GST-RXR LBD/6His RAR LBD was prepared from E.coli cells and purified by gel filtration chromatography through a Superdex S-200 column (Pharmacia). In vitro $^{35}$[S]Methionine-labeled SMRT and mSin3A and B, and HDAC1 were synthesized using the indicated CMX plasmids as templates in a coupled transcription-translation system TNT (Promega). In vitro translated, $^{35}$S-Methionine labeled SMRT was incubated with equal amounts of either GST or GST-RXR LBD/6 His-RAR LBD heterodimer in the absence or presence of 5 TM ATRA. Radiolabeled GAL4-DBD fusion of PAH–4 of mSin3A was incubated either with GST or GST-RXR LBD/6 His-RAR LBD heterodimer and labeled SMRT in the absence or presence of 5 TM all-trans retinoic acid (atRA) for 2h at 4° C. Bound proteins were eluted with 1X SDS PAGE buffer and separated on a 7.5 or 12.5% SDS-PAGE. Gels were fixed, dried and exposed to film. Both mSin3A (PAH1–4) and SMRT are retained on the matrix in the absence of ligand and are released in a retinoic acid dependent fashion.

Genetic studies from yeast suggest that Sin3 repression can function through an Rpd3 dependent pathway (Stillman et al., Genetics 136:781–788 (1994)). Using GST fusions of SMRT 38–448 (SRD-1) and SMRT 548–811 (SRD-2) as affinity matrices, both SRD-1 and SRD-2 are able to form ternary complexes with $^{35}$S Methionine labeled mSin3A and HDAC1. Interestingly HDAC1 appears to interact more strongly with the SRD1/Sin3 complex than SRD2/Sin3. Together, these observations confirm that RAR/RXR heterodimers form a hormone-sensitive complex with SMRT, HDAC1, and mSin3A.

EXAMPLE 5

Functional Interaction Between HDAC1 and SMRT

Figure 2A:
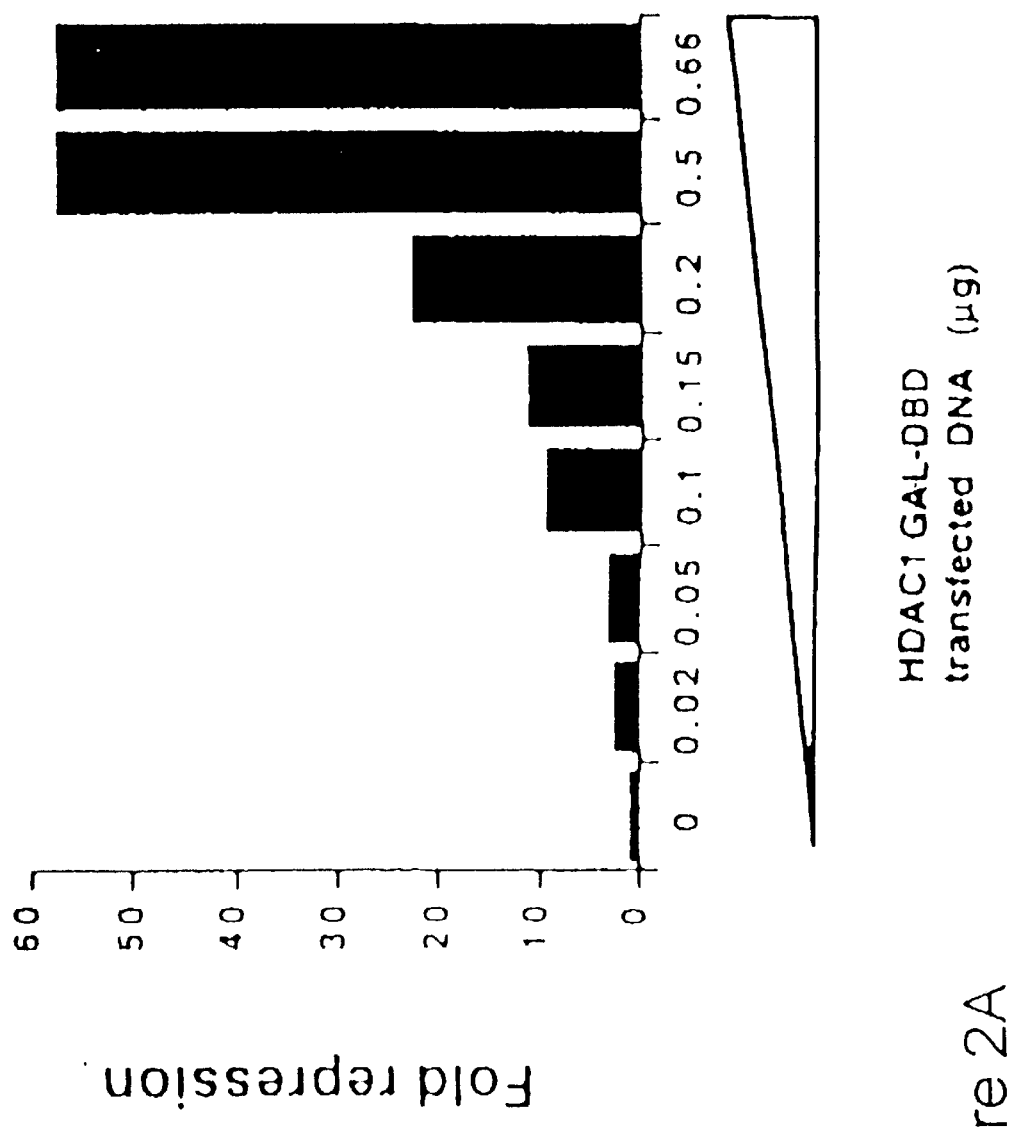
FIG. 2(A) shows that DNA bound HDAC1 (HDAC-GAL4) is a potent repressor of transcriptional activation, resulting in a 60 fold repression of basal activity.

If HDAC1 is a mediator of SMRT silencing, then direct recruitment of HDAC1 to a heterologous promoter should result in repression of basal activity. This prediction was tested by fusing HDAC1 to the GAL4 DBD and assaying its effect on the basal activity of the GAL4-dependent reporter in transient transfection assays in CV-1 cells. The reporter gene contained GAL4 binding sites upstream of a minimal TK promoter fused to luciferase gene (pMH100-TK-luc). Normalized luciferase activity was determined and fold repression (relative to GAL4-DBD alone) was calculated. FIG. 2A shows that HDAC1-GAL4 is a potent repressor of transcriptional activation resulting in a 60-fold repression of basal activity. Similar results were recently reported by Yang, W-M. et al., Nature 382:319–324 (1996) using mammalian homologs of Rpd3.

Figure 2B:
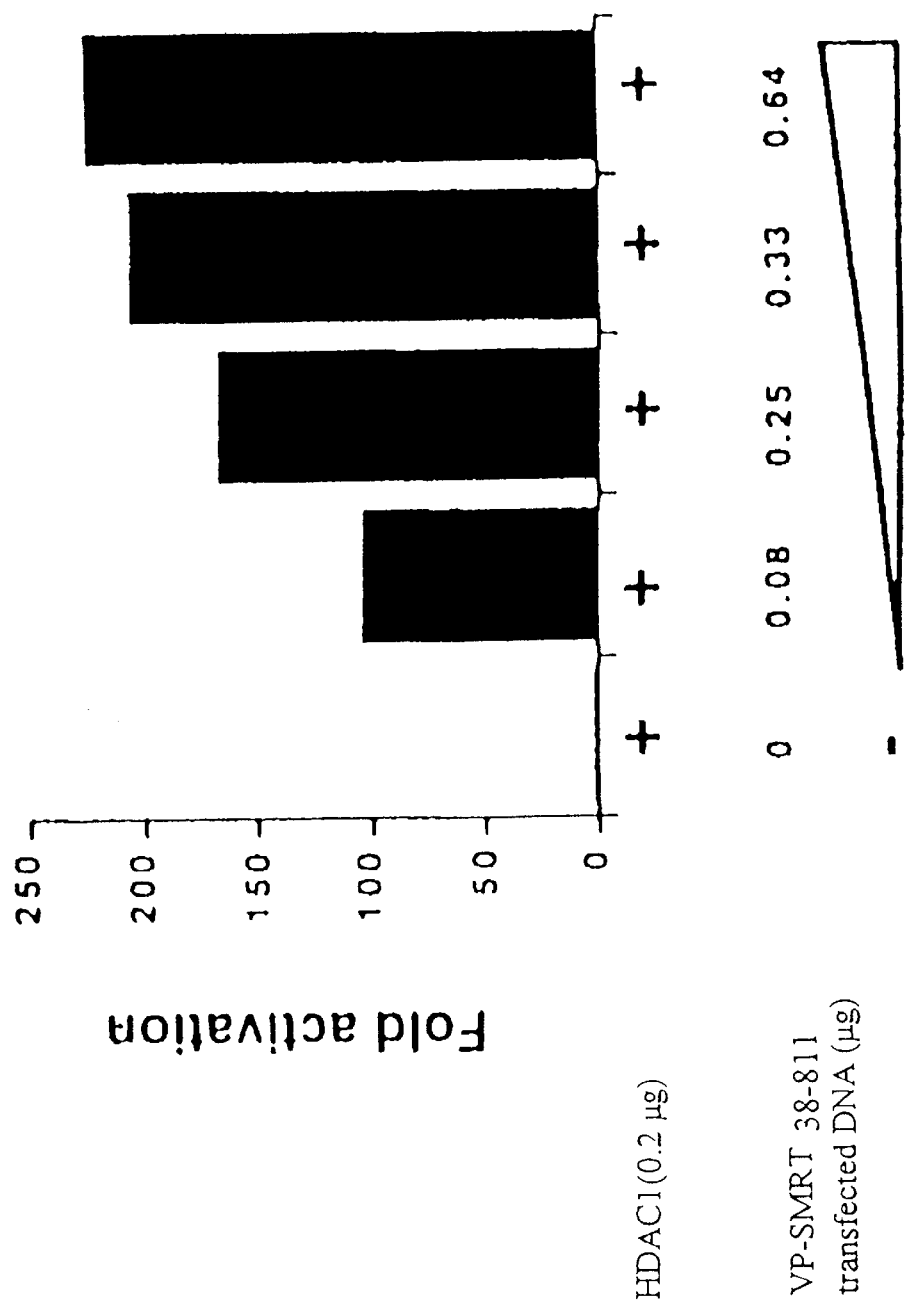
FIG. 2(B) shows the relief of HDAC1 dependent repression by VP-SMRT 38–811.

To test whether HDAC1 and SMRT form a complex in mammalian cells, a fusion of SMRT 38–811 to the Herpes simplex VP16 activator domain was tested with HDAC1-GAL4 in a mammalian two-hybrid assay. Transient transfections were carried out (as described above to determine the effect of HDAC1 on the basal activity) with a fixed amount (0.2 μg) of HDAC1-GAL4-DBD and increasing amounts of the VP-fusion of SMRT 38–811. FIG. 2B shows that as increasing amounts of VP-SMRT are co-expressed with HDAC1-GAL4, the transcriptional activity of the repressed promoter increases dramatically whereas VP-SMRT alone has no effect on the reporter alone or co-expressed with GAL4 DBD. Activation above basal strongly supports the contention that VP-SMRT must be recruited to the promoter by HDAC1-GAL4 (FIG. 2B). Transient transfection assays identical to the ones described above (see FIG. 2B) were carried out with the indicated amounts of HDAC1-GAL4-DBD and VP-SMRT 38–811 in the presence of increasing amount of SMRT (full length) or SMRT 982–1495 expression vectors.

Figure 2C:
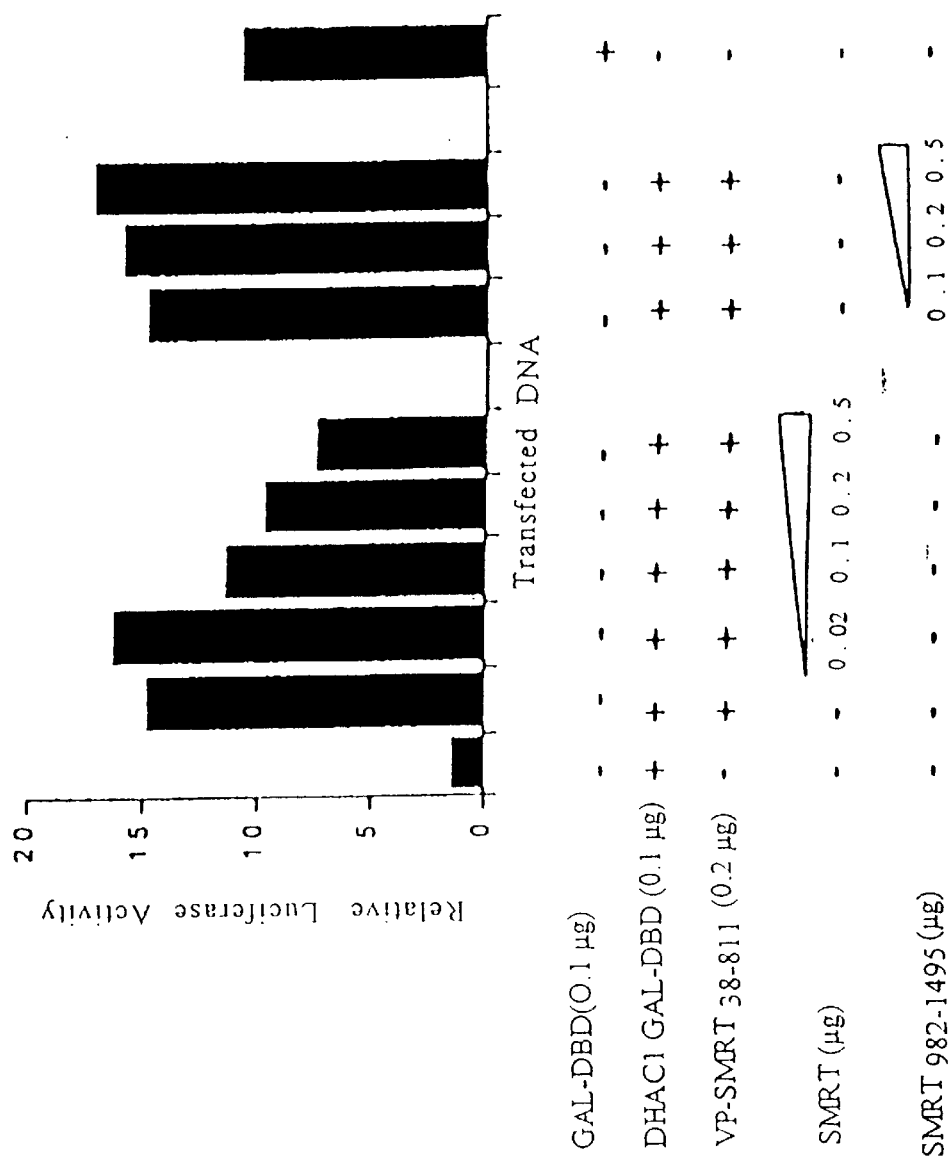
FIG. 2(C) illustrates that full length SMRT (but not SMRT 982–1495) squelches the relieving effect of VP-SMRT 38–811 on HDAC I dependent transcriptional repression.

As shown in FIG. 2C, transfection of increasing amounts of full length SMRT displaces the VP-SMRT activator and re-establishes repression to an approximately 50% level (lane 6). As a control, co-transfection of the carboxy terminal domain of SMRT fails to squelch the VP-SMRT/HDAC1 interaction. These results demonstrate both direct and functional association between HDAC1 and SMRT and demonstrates the strong repressive function of a promoter tethered histone deacetylase.

EXAMPLE 6

Retinoic Acid and Trichostatin A Synergize in Cell Differentiation

If HDAC is a critical component of receptor function then addition of a deacetylase inhibitor, such as Trichostatin A (TSA) (Taunton et al., Science 272:408–411 (1996)) would be expected to relieve transcriptional repression, resulting in a promoter that is likely to be more sensitive to the addition of hormone. This prediction was tested by studying the effect of TSA on the differentiation of myeloid leukemia (HL-60) cells (Collins, Blood 70:1233–1244 (1987)) following a high dose ( 100 nM) 9-cis RA treatment. A hallmark of this process is the appearance of cell surface differentiation markers CD14 and CD11b (Brackman et al., Leukemia Research 19:57–64 (1995)). HL-60 cells cultured in RPMI 10% FBS were plated at a density of $2 \times 10^5$/ml in RPMI 2% FBS treated with 9-cis RA (Sigma) and/or Trichostatin A (TSA) (Waco Pure Chemical Industries) for 72 hours and then incubated with R-phycoerythrin (RPE) conjugated anti-human C3bi receptor (CD11b) (DAKO) or RPE-conjugated monoclonal mouse anti-human CD 14 (DAKO) antibodies for 60 minutes on ice. Cells were washed twice with PBS 0.5% BSA and analyzed on a FACScan flow cytometer (Becton Dickinson). The expression of cell surface antigens (CD11b and CD14) were monitored.

Figure 3A:
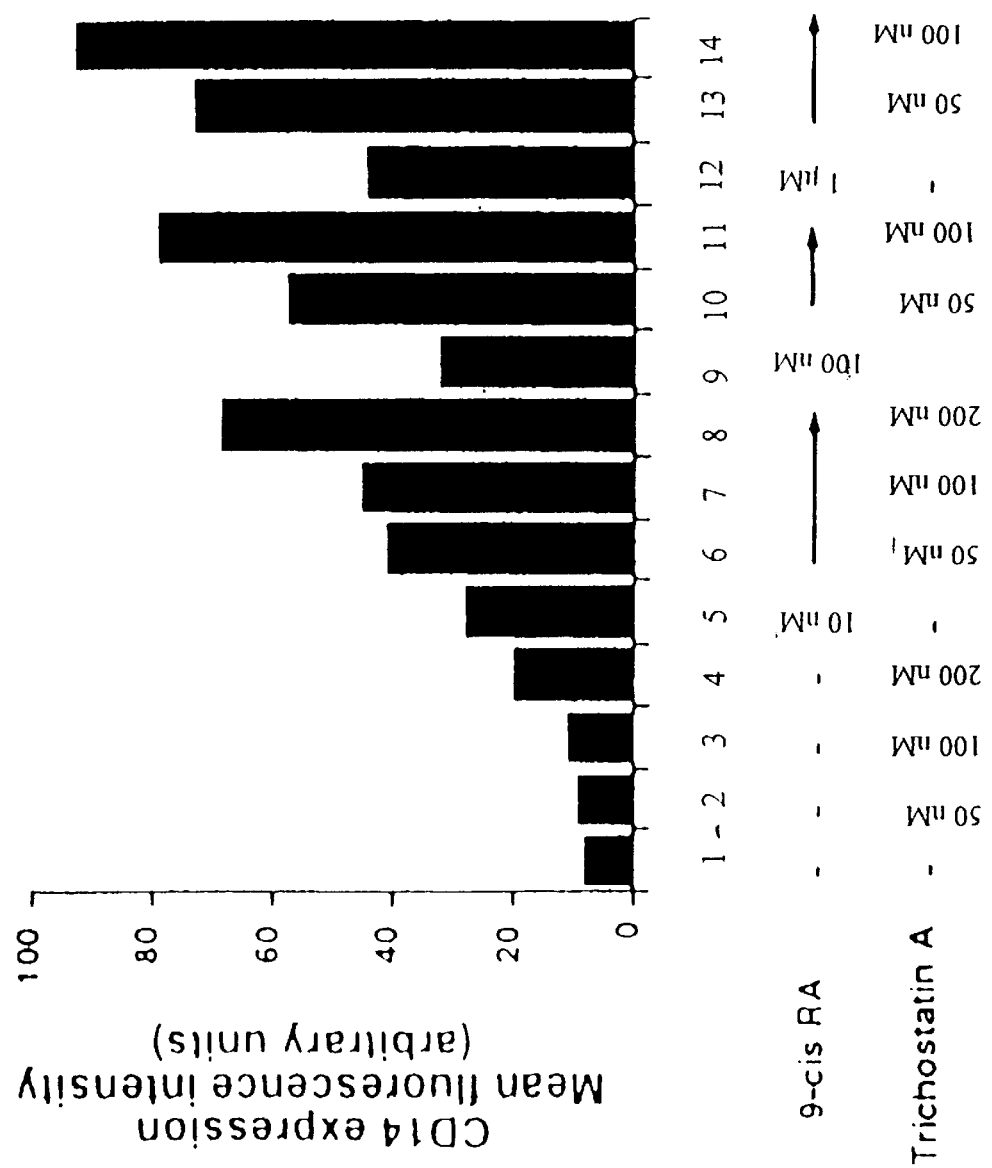
FIG. 3(A) shows the potentiation of 9-cis retinoic acid (9-cis RA) induced differentiation by the histone deacetylase inhibitor Trichostatin A (TSA). CD14 expression levels of HL-60 cells treated with the indicated amount of Trichostatin A (TSA), 9-cis RA alone or in combination were determined by flow cytometry. The mean fluorescence intensities (FL2) from a representative experiment are presented.
Figure 3B:
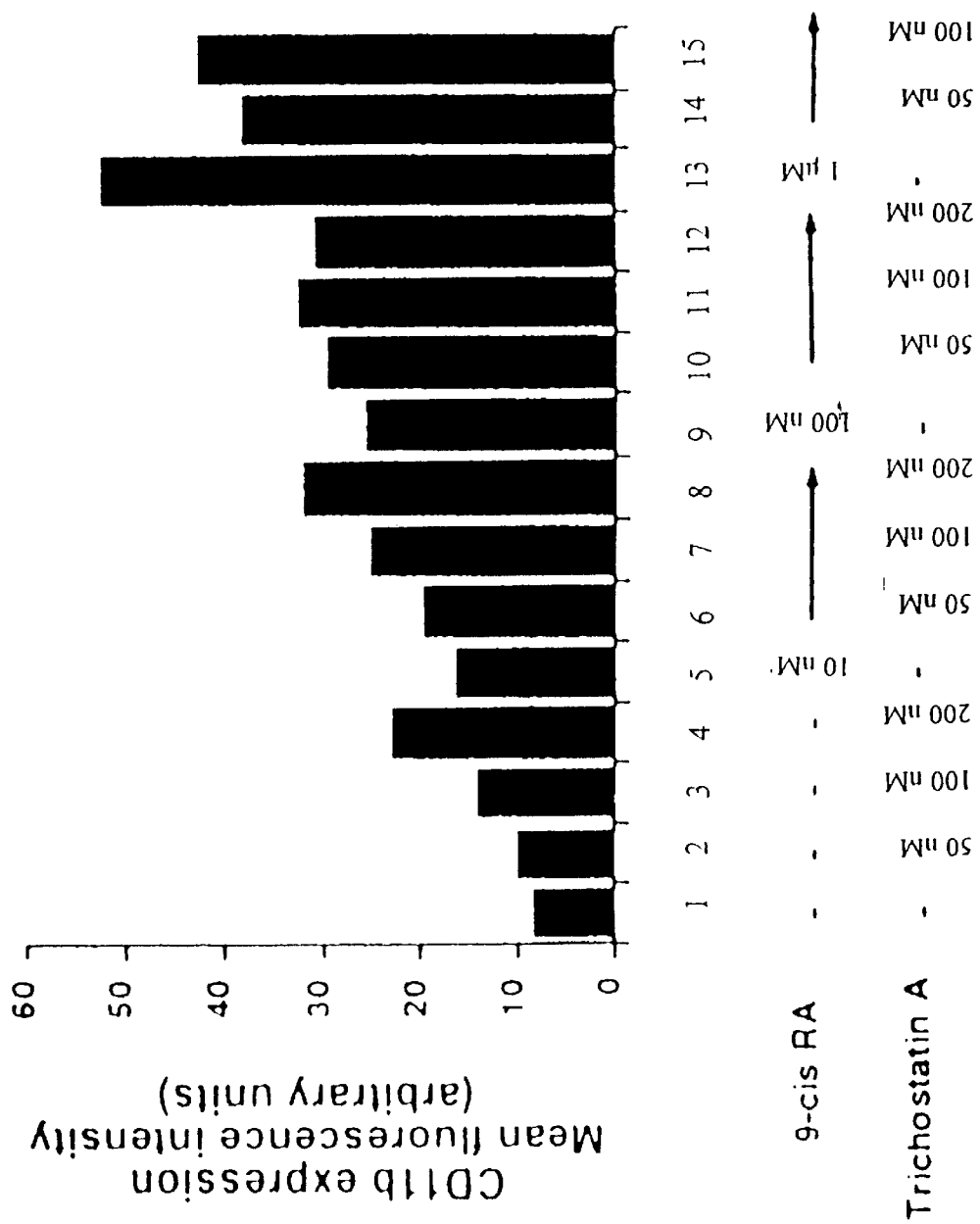
FIG. 3(B) illustrates CD11b expression levels on HL-60 cells treated with the indicated amount of TSA or 9-cis RA alone or in combination.
Figure 3C:
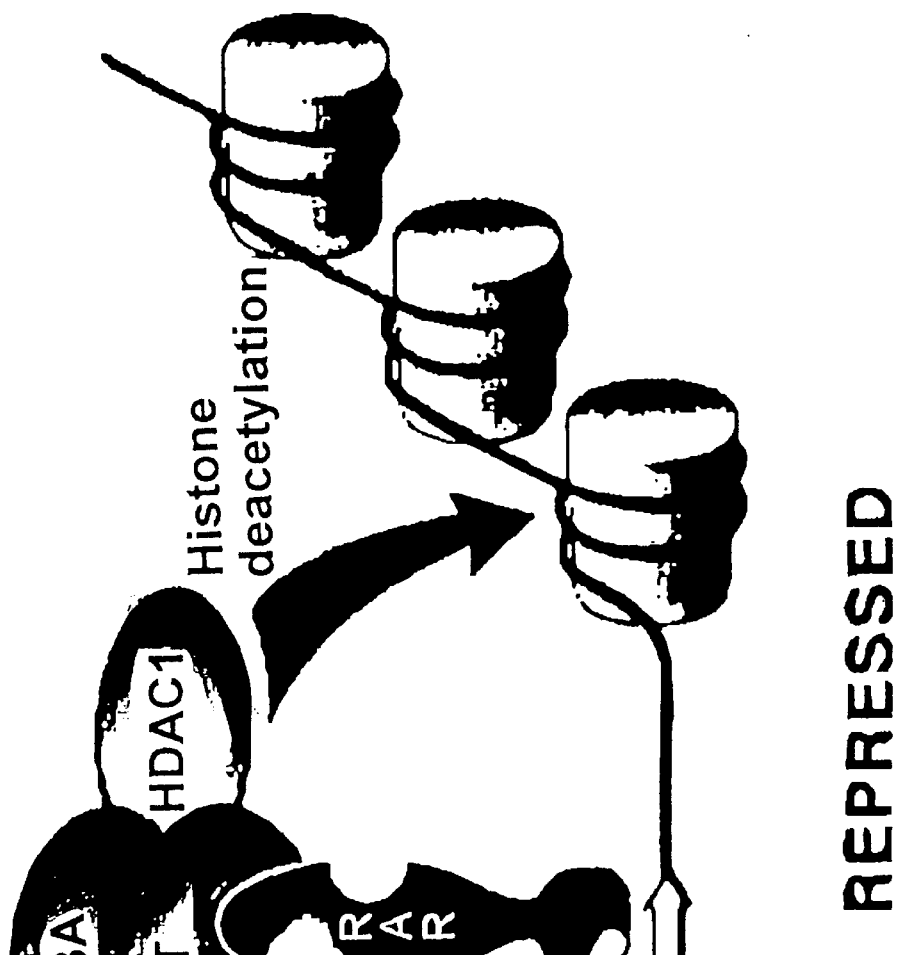
FIG. 3(C) diagrams hormonal targeting of nuclear complexes to chromatin template. In the absence of hormone, a SMRT, mSin3A and HDAC1 complex associates with unliganded receptor heterodimers. In this complex, histone deacetylase activity creates a repressed chromatin environment.

100 nM TSA showed a minimal effect on the CD14 marker while a suboptimal dose (10 nM) of 9-cis RA resulted in modest stimulation (FIG. 3A). However, addition of both TSA and 10 nM 9-cis RA resulted in dramatic enhancement of CD14 expression to levels higher than that following 100 nM 9-cis RA treatment. Surprisingly the high dose 9-cis RA treatment was also enhanced by TSA. Similar results were seen with the CD11b marker, although in this case low doses of TSA partially activated gene expression (FIG. 3B). Again, the combination of TSA and 9-cis RA proved to be cooperative at both high and low doses. While low levels of TSA were used to maintain dependence on retinoids for differentiation, a contribution to CD14/11b expression by other deacetylase sensitive factors cannot be excluded. Nonetheless, this work is consistent with there being a role for histone deacetylase in nuclear receptor signaling.

EXAMPLE 7

Association of SMRT with PLZF

Recombinant proteins were obtained as follows and in vitro protein interaction assays were carried out as follows. GST-PLZF and GST-SMRT fusion proteins were produced from E. Coli DH5a or BL-21 cells and purified by glutathione-Sepharose 4B affinity chromatography. Bound proteins were eluted with 15 mM glutathione. Purified proteins were then reloaded on glutathione-Sepharose 4B beads and used as affinity matrices. Protein interaction assays were performed in G buffer (20 mM Tris, 7.9, 150 mM KCl, 1 mM EDTA, 4 mM $MgCl_2$, 0.26 NP-40, 10% Glycerol) at 4° C. for 60 min with gentle rocking. The beads were washed five times with G buffer and bounded proteins were eluted in SDS sample buffer, separated by SDS-PAGE and visualized by autoradiography.

$^{35}$S-labelled N-SMRT or C-SMRT proteins were incubated with immobilized glutathione-S-transferase (GST)-RARα or GST-PLZF (amino acids 7–118) affinity matrices and analyzed by SDS-PAGE together with 20% of the input. The matrix-bound fusion protein of GST with the BTB (Bric-a-brac/Tramtrack/Broad Complex) domain of PLZF (GST-PLZF), was able to retain radiolabelled N-SMRT (amino acids 1–981) or C-SMRT (amino acids 982–1,495) proteins, while GST-RARα retained only C-SMRT as expected (Chen et al. (1995) Nature 377:454–457).

Figure 4A:
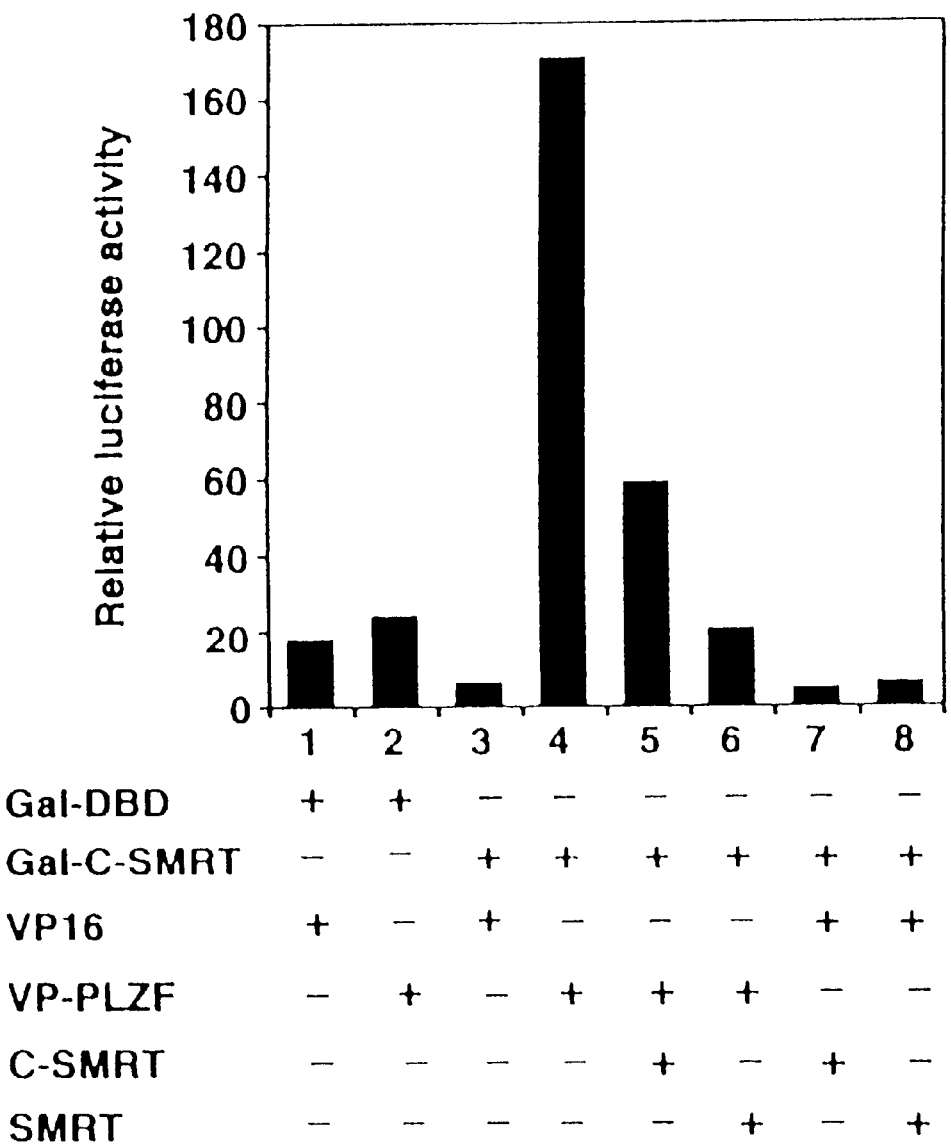
FIG. 4(A) depicts the interaction between SMRT and PLZF in a mammalian two-hybrid assay in CV1 cells. The TK-MH100-Luc reporter used has four GAL4 binding sites.

The association of PLZF with SMRT in intact cells was demonstrated using a mammalian two-hybrid assay. VP16-PLZF, but not VP-16, stimulated UAS reporter expression 25-fold when cotransfected with GAL-C-SMRT (FIG. 4(A)). Cotransfection of either SMRT or C-SMRT expression vectors reduced the activation, by inhibiting the activity of VP16-PLZF. Similar interaction was also observed between PLZF and the SMRT-related corepressor, N-CoR (Horlein et al. (1995) Nature 377:397–404).

Since it has been shown that the BTB domain directs PLZF and PLZF-RARα into speckle-like nuclear structures (Licht et al. (1996) Oncogene 12:323–336; Dong et al. (1996) Proc. Natl Acad. Sci. USA 93:3624–3629), SMRT was examined to determine whether it localizes to the same structures. HA-tagged PLZF or PLZF-RARα and SMRT were expressed in 293T cells and their subcellular localization was determined by immunohistochemical techniques.

For in vitro immunoprecipitation, in vitro translated proteins were incubated together with 10 μg/μl anti-HA antibody in G buffer at 4° C. for 60 min. Immunocomplexes were isolated by incubation with protein A-agarose, washed four times with G buffer, analyzed by SDS-PAGE and visualized by autoradiography. For in vivo immunoprecipitation, $2 \times 10^7$ CV1 cells were transfected with 10 μg of appropriate plasmids and harvested in ice-cold PBS, 24 hours after transfection. Cells were lysed by hypotonic shock and the nuclear pellet was resuspended in IP buffer (PBS, 10 mM NaF, 25 mM β-glycerolphosphate, 0.1% NP-40, 0.5 mM PMSF plus protease inhibitors) and disrupted by mild sonication.

Immunoprecipitation was performed at 4° C. overnight in the presence and absence of 5 μM ATRA. Immunocomplexes were resolved by SDS-PAGE and analyzed by immunoblotting. Immunohistochemistry was done as previously described (Dyck et al. Cell 76:333–343 (1994). PLZF and PLZF-RARα were detected by the mouse anti-HA antibody following instructions from the manufacturer (Boehringer Mannheim).

Figure 4B:
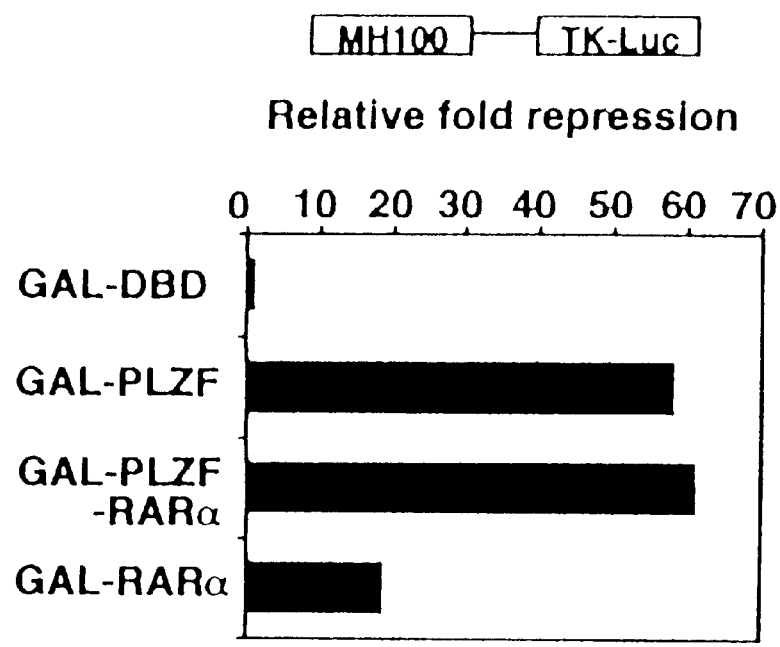
FIG. 4(B) shows the transcriptional repression by GAL-PLZF and GAL-PLZF-RARα in CV1 cells.

It is apparent from these experiments that PLZF or PLZF-RARα and SMRT colocalize to the same nuclear compartments. These nuclear structures are not PODs (PML oncogenic domains; Dyck et al. (1994) Cell 76:333–343; Weis et al. (1994) Cell 76:345–356) as judged by anti-PML and anti-Sp100 staining. Consistent with their ability to interact with SMRT, both PLZF and PLZF-RARα are very potent transcriptional repressors (FIG. 4(B)) when they are artificially recruited to promoters via fusion to GAL4 DNA binding domain (GAL4-DBD).

Recently, it was demonstrated that SMRT or N-CoR associates with mSin3 and histone deacetylases (HDACs) to mediate transcriptional repression by nuclear receptors and Mad/Max complex (Nagy et al. (1997) Cell 89:373–380; Heinzel et al. (1997) Nature 387:43–48; Alland et al. (199–7) Nature 387:49–55). To investigate whether the PLZF/SMRT complex can also recruit mSin3 and histone deacetylases, anti-HA immunoprecipitation was performed using in vitro translated HA-PLZF, SMRT, mSin3A and HDAC-1 proteins.

Radiolabelled SMRT, mSin3A and HDAC-1 were co-immunoprecipitated with PLZF. The PLZF/SMRT complex associated with mSin3A (PAH 1–4) and HDAC-1, suggesting they formed a quaternary complex. The observation that SMRT interacts with PLZF, together with the observation that SMRT interacts with LAZ3/BCL6, provide the first evidence that oncogenes containing the BTB domain utilize the same repression pathway as nuclear receptors and Mad/Max. Furthermore, this domain alone, which has been shown to be required for the oncogenic function of PLZF-RARα (Horlein et al. (1995) Nature 377:397–404; Ruthardt et al. (1997) Mole. Cell. Biol. 17:4859–4869), is sufficient to interact with SMRT and recruit the histone deacetylase complex.

EXAMPLE 8

Regions of SMRT Involved in Interaction With PLZF

Figure 5:
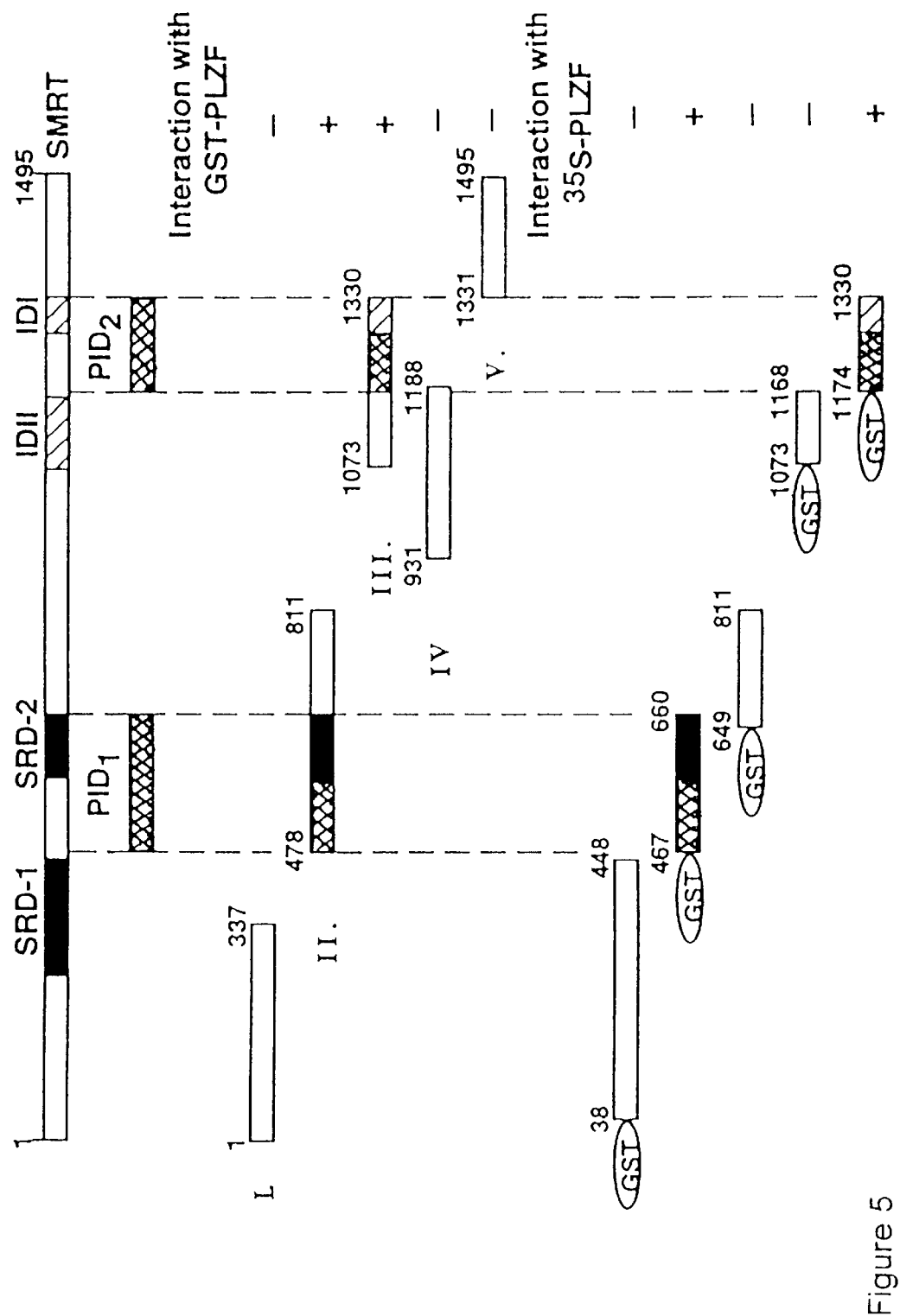
FIG. 5 provides a schematic representation of SMRT domain structures and the mutants used: "SRD-1" and "SRD-2" refer to SMRT repression domains 1 and 2, respectively; "IDI" and "IDII", refer to nuclear receptor interaction domains I and II, respectively; $PID_1$ and $PID_2$, refer to N- and C-terminal PLZF (promyelocytic leukemia zinc finger) interaction domains, respectively. Mutants I to V were used for in vitro translation.

To map regions of SMRT that bind PLZF, a series of $^{35}$S-labelled fragments of SMRT were generated and tested for their interaction with GST-PLZF affinity matrix. Two PLZF interacting regions in SMRT were identified at amino acids 478–811 and 1,073–1,330 (FIG. 5). Indicated SMRT mutants were labelled with $^{35}$S and incubated with immobilized GST-PLZF affinity matrix in pull-down assays. Further mapping using a series of GST-fusions of SMRT, tested for interaction with $^{35}$S-PLZF, delineated two minimal PLZF interaction domains encompassing amino acids 467–660 ($PID_1$) and 1,174–1,330 ($PID_2$) respectively (FIG. 5).

EXAMPLE 9

Role of SMRT in the Oncogenic Function of PLZF-RARα

Figure 6A:
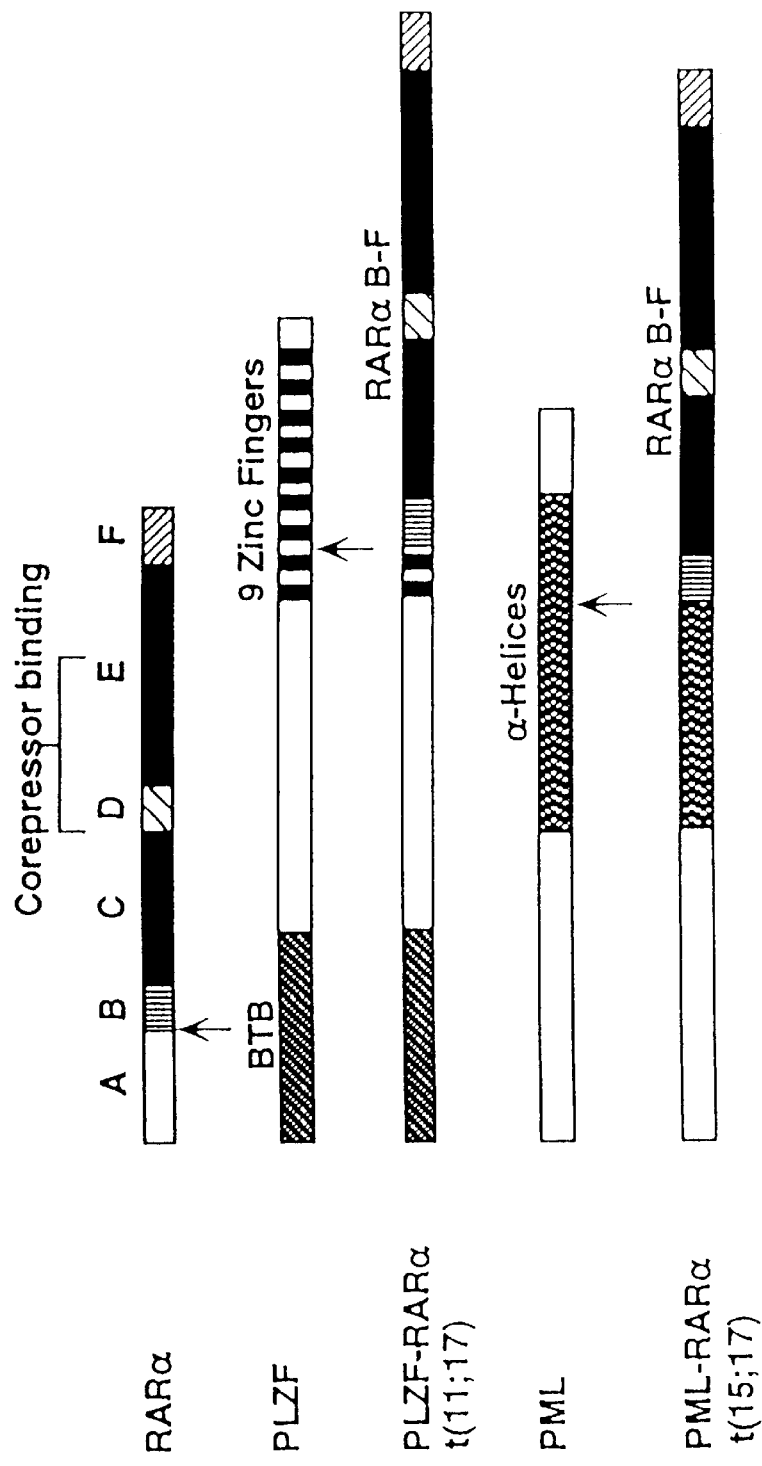
FIG. 6(A) provides a schematic representation of the chromosomal translocations that generate PLZF-RARα and PML-RARα (promyelocytic leukemia—RARα).

PML-RARα and PLZF-RARα are the two major oncogenic fusion proteins identified in APL patients (FIG. 6(A)). Affinity matrices were employed to determine whether $^{35}$S-labelled RARα or PLZF-RARα would interact with immobolized GST-SMRT-IDII (amino acids 1,073–1,168) and GST-SMRT-$PID_2$ protein in the presence or absence of 5 μM ATRA. Binding of both radiolabelled RARα and PLZF-RARα to GST-SMRT-IDII is significantly reduced when all-trans retinoic acid (ATRA) is present, suggesting that the association of SMRT with the RAR portion of PLZF-RARα is ligand-sensitive. In striking contrast, PLZF-RARα, but not RARα, binds GST-SMRT-$PID_2$ in a ligand-insensitive manner, suggesting that ligand binding to the RAR moiety of PLZF-RARα does not affect association of SMRT with the PLZF moiety.

To confirm these in vitro results, immunoprecipitation assays are performed from CV1 cell extracts transfected with HA-tagged either RARα or PLZF-RARα, followed by immunoblotting to detect specifically associated SMRT. This analysis revealed that the amount of SMRT which associates with RARα is greatly reduced in the presence of ATRA (5 μM) while the amount of SMRT associated with PLZF-RARα is largely unaffected by RAR ligands. These results indicate that fusion of PLZF to RAR generates a receptor that associates with SMRT in the presence of retinoids.

GAL4-DBD fusions of RARα or PLZF-RARα were transfected into CV1 cells and examination of their RA-activation on UAS reporters. CV1 cells were transfected using DOTAP transfection reagents (Boehringer Mannheim). Luciferase activity of each sample was normalized against internal control β-galactosidase activity (Nagy et al. (1997) Cell 89:373–380). Each transfection was carried out in triplicate and repeated at least three times. When indicated, transfected cells were treated with ATRA alone for 36 hours or 16 hours with ATRA plus histone deacetylase inhibitors.

Figure 6B:
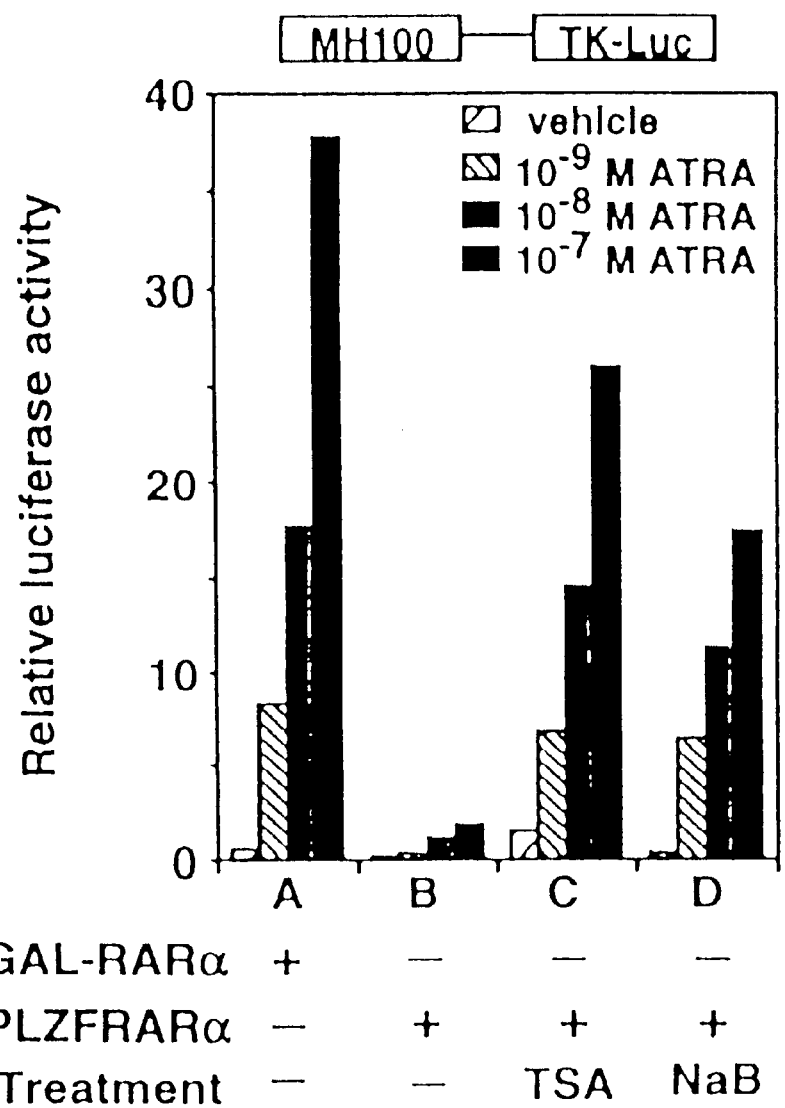
FIG. 6(B) illustrates activation of GAL-PLZF-RARα by histone deacetylase inhibitors Trichostatin A (TSA) (150 nM) or sodium butyrate (NaB) (5 mM) synergized with all-trans retinoic acid (ATRA).

As expected, GAL-PLZF-RARα poorly responded to ATRA compared to GAL-RARα (FIG. 6(B), columns A and B), presumably due to the association with SMRT. Remarkably, treatment with histone deacetylase inhibitors Trichostatin A (TSA) or Na-butyrate (NaB), which inhibit SMRT-mediated repression (Nagy et al. (1997) Cell 89:373–380; Heinzel et al. (1997) Nature 387:43–48), relieved repression by GAL-PLZF-RARα and synergized with ATRA to activate reporters (columns C and D).

Figure 6C:
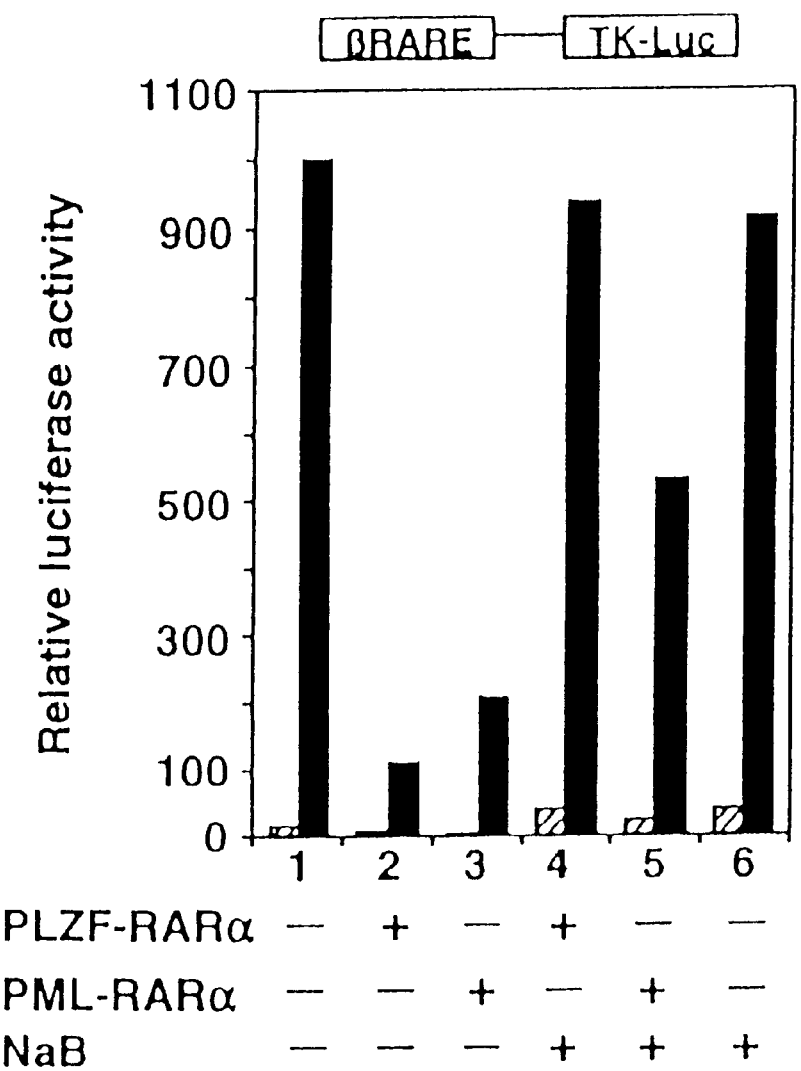
FIG. 6(C) illustrates the relief by NaB (5 mM) of transcriptional inhibition by PLZF-RARα and PML-RARα on TK-βRAREx2-Luc reporters in the presence and absence of 100 nM ATRA, respectively.

It was then sought to determine whether similar effects can be seen on native RA-response elements. As shown previously, exogenous expression of PLZF-RARα or PML-RARα inhibits RA-activation mediated by endogenous RARs on βRARE reporters (FIG. 6(C); de Thé et al. (1991) Cell 66:675–684; Kastner et al. (1992) EMBO J. 11:629–642; Chen et al. (1994) Proc. Natl Acad. Sci. USA 91:1178–1182; Licht et al. (1996) Oncogene 12:323–336; Rousselot et al. (1994) Oncogene 9:545–551). Once again, histone deacetylase inhibitor NaB was able to restore nearly full RA activation in the presence of PLZF-RARα. Interestingly, NaB also partially, relieves transcriptional inhibition by PML-RARα, suggesting that SMRT and histone deacetylases mediates the oncogenic function of PML-RARα as well.

EXAMPLE 10

Role of SMRT in the oncogenic function of PML-RARα

PML-RARα oncogene blocks myeloid differentiation in vitro and in vivo (Grignani et al. (1993) Cell 74:423–431; Brown et al. (1997) Proc. Natl Acad. Sci. USA. 94:2551–2556). In contrast to PLZF-RARα, however, this block can be overcome by high doses of RA. It has been proposed that PML-RARα causes leukemia by interfering with either the RAR or PML dependent differentiation pathways (Dyck et al. (1994) Cell 76:333–343; Weis et al. (1994) Cell 76:345–356; Grignani et al. (1994) Blood 83:10–25). Recently, it has been demonstrated that DNA binding and dimerization of PML-RARα are required for its oncogenic function (Grignani et al. (1996) EMBO J. 15:4949–4958).

The fact that SMRT associates with PML-RARα (Sande, S. And Privalsky, M. L.(1996) Mol. Endo. 10:813–825) and the ability of NaB to partially relieve transcriptional inhibition by PML-RARα prompted investigation to determine whether co-repressors contribute to the pathogenesis of t(15;17) APL. In vitro translated receptors and purified GST fusion proteins were incubated with 1 μg poly(dI:dC) on ice in a 18 μl reaction containing 100 mM KCl, 6% glycerol, 16.7 mM Tris (pH 7.5), 0.1% NP-40, 1 mM DTT and ATRA as indicated. $^{32}$P-labeled double-strand DR5 (5' TCGACT-CaggtcaCCACGaggtcaGAGTC 3'; SEQ ID NO:3) oligonucleotide probes (150,000 cpm) were then added and incubation was continued for 30 min at room temperature. The protein-DNA complexes were then resolved on a 4.5% native polyacrylamide gel and visualized by autoradiography. As with PLZF-RARα, interaction of radiolabelled RARα or PML-RARα affinity matrix revealed that both radiolabelled RARα and PML-RARα were retained on the GST-SMRT (amino acids 1,073–1,330) affinity matrix. Surprisingly, while ATRA effectively dissociated SMRT from RARα, it only weakly affected the PML-RARα/SMRT complex.

Since PML-RARα forms stable homodimers in vitro and in vivo on retinoid response elements (Perez et al. (1993) EMBO J. 12:3171 3182; Jansen et al. (1995) Proc. Natl Acad. Sci. USA 92:7401–7405), gel mobility shift assays were used to examine the association of GST-SMRT-IDII with either RARα/RXRα heterodimers or PML-RARα homodimers on DR5 elements in the presence or absence of ATRA. This analysis reveals that substantially higher concentrations of ATRA were required to dissociate SMRT from DNA-bound PML-RARα than from RAR. Similar results were also obtained with PML-RARα/RXRα heterodimers.

Figure 7A:
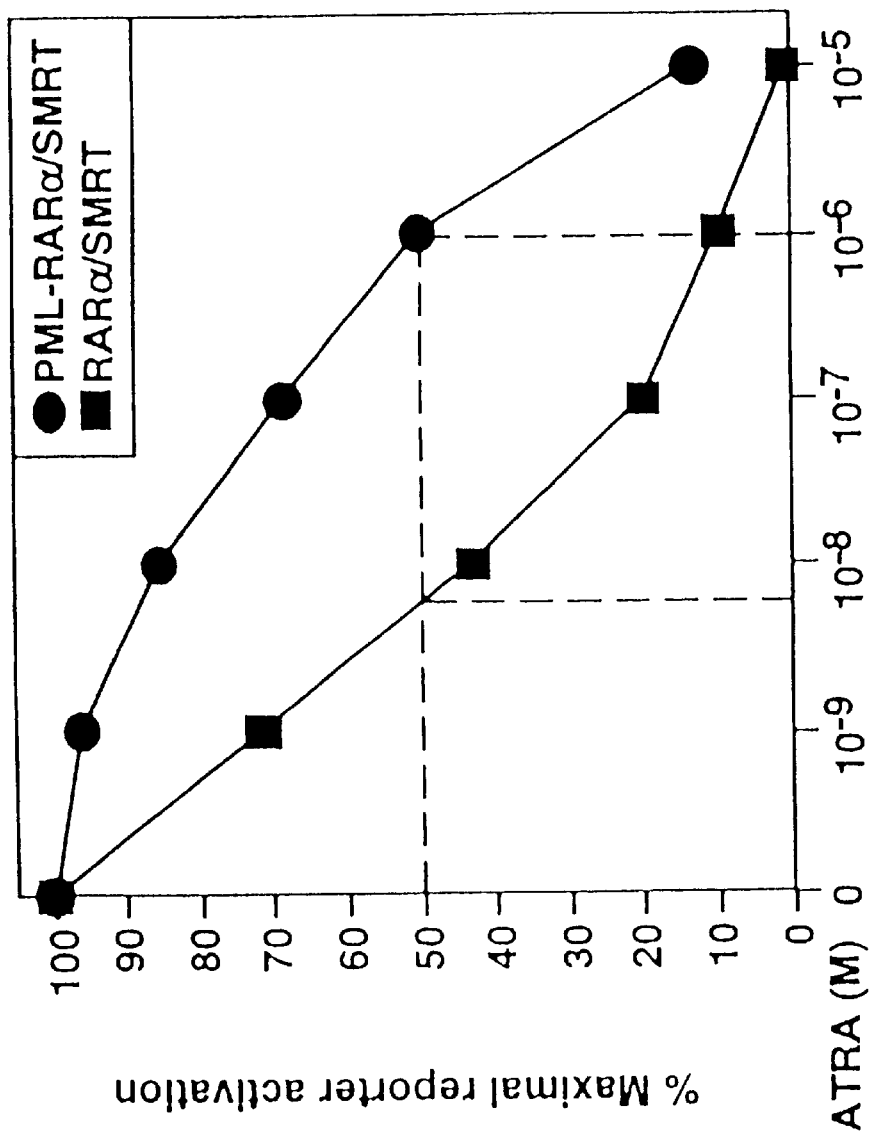
FIG. 7(A) provides a comparison of ATRA dose-dependent interaction between SMRT and RARα or PML-RARα in CV1 cells transfected with GAL-C-SMRT and VP-F-RARα or VP-PML-RARα.

The RA dose-dependent interaction between SMRT and PML-RARα in vivo was examined using a mammalian two-hybrid assay (FIG. 7 (A)). Strikingly, this interaction appeared to be 100~200 fold less sensitive to ATRA than the interaction between SMRT and RARα ($EC_{50PML-RAR}$ 1 μM and $EC_{50RAR}$ 5 nM).

Together, these results suggest that fusion of PML to RARα generates a receptor with significantly decreased ability to release SMRT upon ligand binding, suggesting that PML modulates the interaction between SMRT and the RAR moiety through an allosteric mechanism since the RA-binding affinity of PML-RARα appears to be normal (Chen et al. (1994) Proc. Natl Acad. Sci. USA 91:1178–1182; Ruthardt et al. (1997) Mole. Cell. Biol. 17:4859–4869) and PML does not physically interact with SMRT, unlike PLZF (Chen et al. (1995) Nature 377:454–457). Alternatively, additional factors associated with the PML moiety may interact with SMRT and interfere with its ability to dissociate from the RAR moiety upon ligand binding.

It is well known that the response of APL patients and APL mice to high-dose retinoid differentiation therapy correlates with the presence of PML-RARα fusion proteins (Brown et al. (1997) PNAS 94:2551–2556; Grignani et al., (1994) Blood 83:10–25), indicating that PML-RARα could serve as RA-dependent activators. Moreover, introduction of PML-RARα into non-responsive hematopoietic cells renders them sensitive to supra-physiological concentrations of retinoids ( Grignani et al. (1993) Cell 74:423–431). This requirement of non-physiological concentrations of retinoids to trigger differentiation could be in fact explained by the impaired dissociation of SMRT. If this is the case, one would predict that inhibition of SMRT-mediated repression could potentiate differentiation-inducing effects of RA.

This prediction was tested utilizing the NB4 cell line established from a patient with t(15;17) APL. NB4, NB4-R4 (Shao et al. (1997) Blood 89:4282–4289), HL-60 and HL-60R (Robertson et al. (1992) Blood 80:1885–1889) cells were cultured in RPMI with 10% FBS. Differentiation effects of ATRA and/or TSA on those cells were assessed using the Nitroblue Tetrazolium (NBT) reduction assay. Differentiation assays with RA and/or TSA were carried out as previously described (Nagy et al. (1997) Cell 89:373–380). NBT assay has been described (Nagy et al. (1995) Mole. Cell. Biol. 15:3540–3551).

Figure 7B:
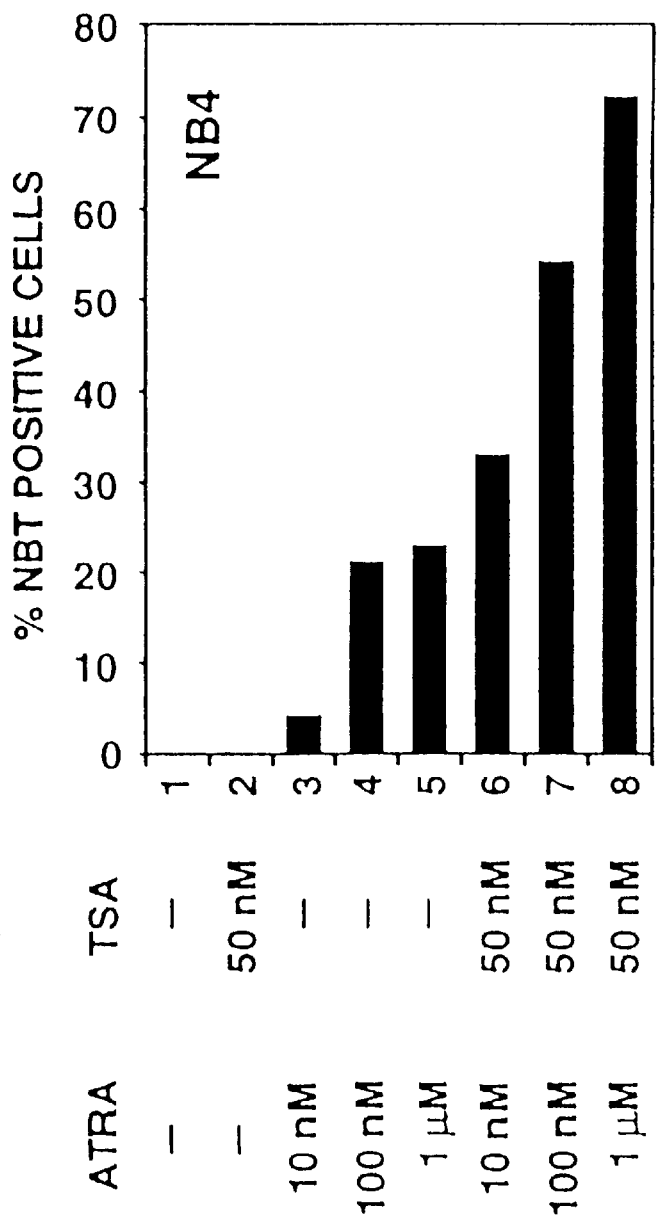
FIG. 7(B) shows the effects of RA on TSA potentiated differentiation of NB4 cells. The Y-axis indicates the percentage of NBT-positive cells after treatments with ATRA and/or TSA for three days.
Figure 7C:
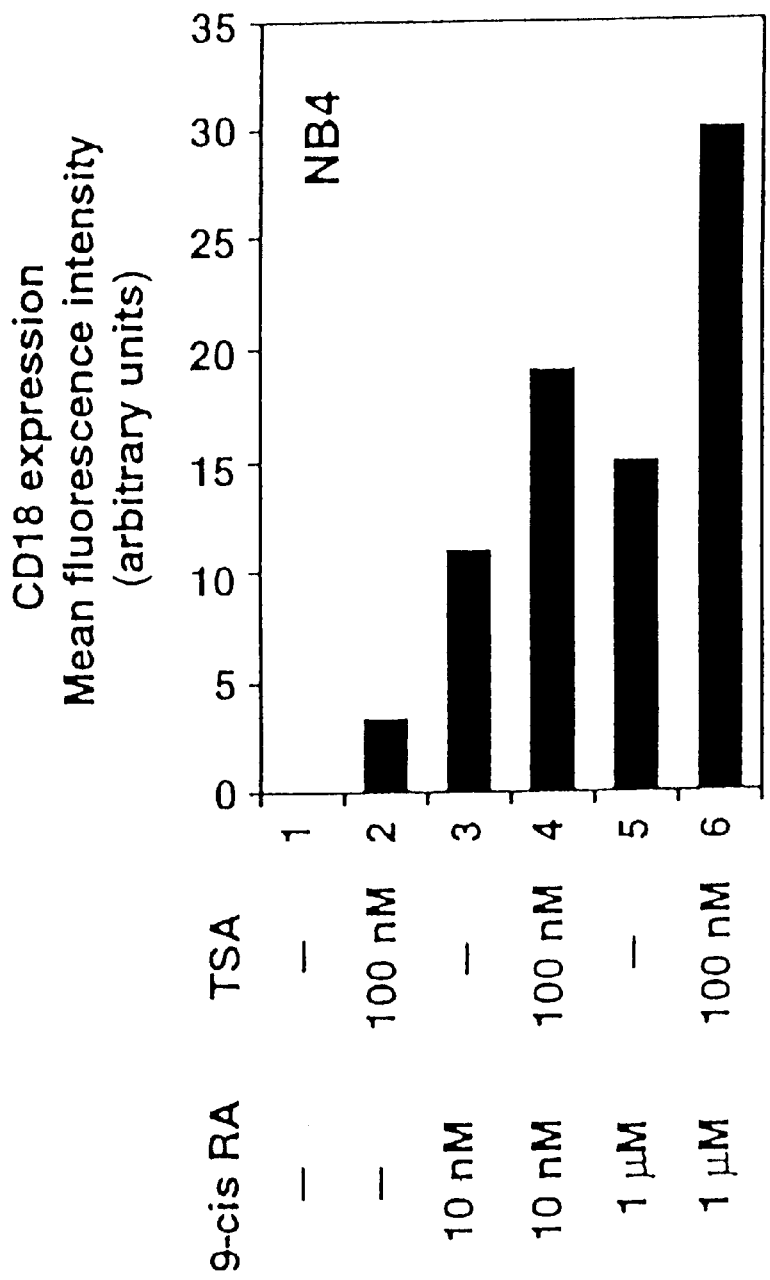
FIG. 7(C) shows CD18 induction after treatments with 9-cis RA and/or TSA for three days as observed by representative flow cytometry analysis. No expression was detected in control cells.

While TSA (50 nM) alone showed no effect, it dramatically enhanced the differentiation effect of ATRA at all concentrations tested (FIG. 7(B)). Flow cytometry analysis of the expression of the early differentiation marker CD18 also revealed a strong stimulatory effect of TSA on RA-induced gene expression (FIG. 7(C)).

For flow cytometry analysis of CD18 expression, the cells were incubated with a FITC-conjugated anti-CD18 antibody (DAKO) in a dilution of 1:500 in PBS (0.5% BSA) followed by extensive washing before analyzing on a FACSCAN flow cytometer (Becton Dickinson). Although histone deacetylase inhibitors are known to have pleiotropic effects on global gene expression, the fact that CD18 is a direct retinoid target gene (Agura et al. (1992) Blood 79:602–609) supports the notion that histone deacetylases are integral components of PML-RARα mediated differentiation. Interestingly, NB4 cells are significantly less sensitive to retinoids than PML-RARα negative myeloid leukemia cells and PML-RARα expressing HL-60 cells are resistant to up to $10^{-7}$ M of ATRA (Rousselot et al. (1994) Oncogene 9:545–551), suggesting that a more tightly bound PML-RARα/SMRT complex blunts the normal retinoid response. This would explain why the inhibition of SMRT-mediated repression by TSA increases the retinoid sensitivity of NB4 cells.

EXAMPLE 11

Role of SMRT in the Development of Acquired Retinoid Resistance in APL Cell Lines Resistance to differentiation by physiological concentrations of RA is a general feature of APL. Although t(15;17) patients initially respond to high doses of retinoid, many of them relapse and develop permanent resistance (Grignani et al. (1994) Blood 83:10–25). Moreover, acquired retinoid resistance in otherwise sensitive HL-60 and NB4 cell lines (HL-60R and NB4-R4) has been traced to dominant negative mutations in RARα (RARα 411) and PML-RARα (m4) respectively, that reduce RA binding (Robertson et al. (1992) Blood 801885–1889; Shao et al. (1997) Blood 89:4282–4289).

Figure 8:
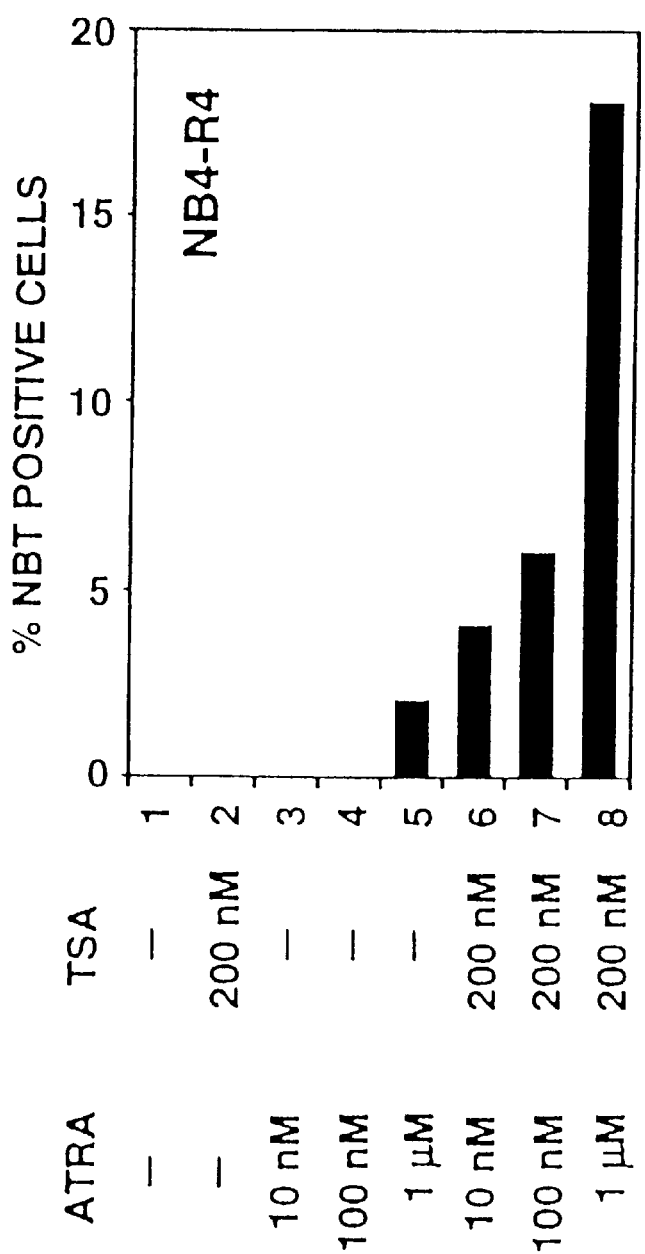
FIG. 8 shows the level of differentiation of the retinoid-resistant NB4-R4 cells induced by the combination of TSA and ATRA. The results are based on NBT-positive cells after treatments with ATRA and/or TSA for three days.

Gel mobility shift analysis of the interaction between GST-SMRT-IDII and RARα 411/RXRα heterodimers on DR5 elements showed impaired dissociation of SMRT from the RARα 411/RXRα heterodimer. GST-SMRT-IDII associated with PML-RARα (m4) homodimers on DR5 elements in the presence of indicated concentrations of ATRA. Furthermore and as expected, treatment of NB4-R4 cells with TSA plus ATRA partially restored hormone-induced differentiation as measured by significant increases of NBT-positive cells (FIG. 8). Note that the percentage of NBT-positive NB4-R4 cells after treatment with 1 mM ATRA and 200 nM TSA (18%) was comparable to what was achieved using 1 mM ATRA alone in parental NB4 cells (23%, FIG. 7(B), lanes 5). Similar results were also obtained with HL-60R.

These findings directly link the association of SMRT with the dominant negative activities of RA-resistant mutants and the development of acquired retinoid resistance.

While the invention has been described in detail with reference to certain preferred embodiments thereof, it will be understood that modifications and variations are within the spirit and scope of that which is described and claimed.

That which is claimed is:

1. A method of treating a subject with a neoplastic disease, said method comprising co-administering to said subject an amount of:
   an inhibitor of a co-repressor, and
   a ligand for a member of the steroid/thyroid superfamily of receptors effective to ameliorate the symptoms of said neoplastic disease, wherein said inhibitor is not sodium butyrate.

2. The method of claim 1 wherein said inhibitor relieves repression of retinoid transcription caused by a co-repressor.

3. The method of claim 2, wherein said co-repressor is selected from SMRT, a histone deacytelase, mSin3A, N-CoR, or combinations thereof.

4. The method of claim 3, wherein said inhibitor is an inhibitor of histone deacetylase.

5. The method of claim 4, wherein said inhibitor of histone deacetylase is selected from the group consisting of Trapoxin and Trichostatin A.

6. The method of claim 3, wherein said inhibitor relieves SMRT-mediated repression.

7. The method of claim 2, wherein said inhibitor disrupts binding of said co-repressor to an onocogene peptide.

8. The method of claim 7 wherein said oncogene peptide is operatively associated with a member of the steroid/thyroid hormone superfamily of receptors.

9. The method of claim 8, wherein said member is RAR.

10. The method of claim 9, wherein said inhibitor relieves repression caused by PML-RARα.

11. The method of claim 7, wherein said oncogenic peptide comprises a BTB domain.

12. The method of claim 11, wherein said BTB domain is derived from LAZ3/BCL6 or PLZF.

13. The method of claim 12, wherein said inhibitor relieves repression caused by PLZF-RARα.

14. The method of claim 1, wherein said subject suffers from APL.

15. The method of claim 1, wherein said ligand is retinoic acid.

16. A method of claim 15, wherein said retinoic acid is all-trans-retinoic acid.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 71 amino acids
       (B) TYPE: amino acid
       (C) STRANDEDNESS: single
       (D) TOPOLOGY: linear (xi) SEQUENCE DESCRIPTION: SEQ ID NO:1:

```
Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
 65                  70
```

(2) INFORMATION FOR SEQ ID NO:2:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:2:

CGGAGGACTG TCCTCCG                                                    17

(2) INFORMATION FOR SEQ ID NO:3:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (xi) SEQUENCE DESCRIPTION: SEQ ID NO:3:

TCGACTCAGG TCACCACGAG GTCAGAGTC                                       29